(12) United States Patent
Papapetridis et al.

(10) Patent No.: US 10,913,928 B2
(45) Date of Patent: Feb. 9, 2021

(54) YEAST STRAINS FOR ETHANOL PRODUCTION

(71) Applicant: DSM IP Assets B.V., Heerlen (NE)

(72) Inventors: Ioannis Papapetridis, Delft (NL);
Antonius Jeroen Adriaan Van Maris, Stockholm (SE); Jacobus Thomas Pronk, Delft (NE)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/471,367

(22) PCT Filed: Dec. 18, 2017

(86) PCT No.: PCT/EP2017/083242
§ 371 (c)(1),
(2) Date: Jun. 19, 2019

(87) PCT Pub. No.: WO2018/114758
PCT Pub. Date: Jun. 28, 2018

(65) Prior Publication Data
US 2020/0095536 A1    Mar. 26, 2020

(30) Foreign Application Priority Data

Dec. 20, 2016 (EP) .................................... 16205338
Feb. 10, 2017 (EP) .................................... 17155525

(51) Int. Cl.
| | | |
|---|---|---|
| *C12N 1/18* | (2006.01) | |
| *C12N 9/00* | (2006.01) | |
| *C12P 7/10* | (2006.01) | |
| *C12N 9/04* | (2006.01) | |
| *C12N 9/02* | (2006.01) | |

(52) U.S. Cl.
CPC ............. *C12N 1/18* (2013.01); *C12N 9/0006* (2013.01); *C12N 9/0008* (2013.01); *C12P 7/10* (2013.01); *C12Y 101/01001* (2013.01); *C12Y 101/01008* (2013.01); *C12Y 102/0101* (2013.01)

(58) Field of Classification Search
None
See application file for complete search history.

(56) References Cited

U.S. PATENT DOCUMENTS

| 6,358,716 B1* | 3/2002 | Bulthuis ................ C12P 7/20 435/159 |
| 9,955,950 B2 | 5/2018 | Kulakowski, Jr. et al. |
| 2005/0153411 A1 | 7/2005 | Wahlbom et al. |
| 2011/0275130 A1* | 11/2011 | Pronk ...................... C12N 1/18 435/165 |
| 2016/0030005 A1 | 2/2016 | Kulakowski, Jr. et al. |
| 2016/0031224 A1 | 2/2016 | Aoki et al. |
| 2016/0208291 A1 | 7/2016 | Klaassen et al. |
| 2016/0312246 A1 | 10/2016 | Pronk et al. |
| 2018/0291404 A1 | 10/2018 | Papapetridis et al. |

FOREIGN PATENT DOCUMENTS

| EP | 2277989 A1 | 1/2011 |
| WO | 2015028582 A2 | 3/2015 |
| WO | 2015028583 A2 | 3/2015 |
| WO | 2015148272 A1 | 10/2015 |
| WO | 2016018813 A1 | 2/2016 |
| WO | 2017060195 A1 | 4/2017 |

OTHER PUBLICATIONS

Bro et al., "In silico aided metabolic engineering of *Saccharomyces cerevisiae* for improved bioethanol production", Metabolic Engineering 8 (2006) 102-111. doi:10.1016/j.ymben.2005.09.007.*
International Search Report for PCT/EP2017/083242 dated Mar. 5, 2018.
Medina et al., "Elimination of glycerol production in anaerobic cultures of a *Saccharomyces cerevisiae* strain engineered to use acetic acid as an electron acceptor", Applied and Environmental Microbiology, vol. 76, 2010, pp. 190-195.
Pickl Andreas et al., "The oxidative pentose phosphate pathway in the haloarchaeon Haloferax volcanii involves a novel type of glucose-6-phosphate dehydrogenase—The archaeal Zwischenferment". FEBS Letters, vol. 1. 589, No. 10, Apr. 28, 2015 (Apr. 28, 2015), pp. 1105-1111.
Gombert et al., "Improving conversion yield of fermentable sugars into fuel ethanol in 1st generation yeast-based production processes" Current Opinion in Biotechnology, 2015, pp. 81-86, vol. 33.
Guadalupe-Medina et al.,"Evolutionary engineering of a glycerol-3-phosphate dehydrogenase-negative,acetate-reducing *Saccharomyces cerevisiae* strain enables anaerobic growth at high glucose concentrations". Microbial Biotechnology, 2013, pp. 44-53, vol. 7.
Henningsen et al., "Increasing Anaerobic Acetate Consumption and Ethanol Yields in *Saccharomyces cerevisiae* with NADPH-Specific Alcohol Dehydrogenase"., Applied and Enviromental Microbiology, Dec. 2015, pp. 8108-8117, vol. 81 No. 23.
Knudsen et al., "Exploring the potential of the glycerol-3-phosphate dehydrogenase 2 (GPD2) promoter for recombinant gene expression in *Saccharomyces cerevisiae*"., Biotechnology Reports, 2015, pp. 107-119, vol. 7.
Van Maris et al., "Intergral engineering of Acetic acid Tolerance in yeast"., Feb. 26, 2014, pp. 1-42.
Pagliardini et al., "The metabolic costs of improving ethanol yield by reducing glycerol formation capacity under anaerobic conditions in *Saccharomyces cerevisiae*". Microbial Cell Factories, 2013, pp. 1-14, vol. 12:29.

(Continued)

*Primary Examiner* — Suzanne M Noakes

(57) ABSTRACT

This invention relates to a recombinant cell, preferably a recombinant yeast cell comprising: a) a gene coding for an enzyme having glycerol-3-phosphate dehydrogenase activity, wherein said enzyme has a cofactor dependency for at least NADP$^+$ and/or for NADPH; b) a gene encoding an enzyme having at least NAD$_+$ dependent acetylating acetaldehyde dehydrogenase activity (EC 1.2.1.10); and c) a mutation or disruption in at least one gene selected from the group of GPD1 and GPD2. Said cell is suitable for ethanol production, has a reduced glycerol production at high ethanol yield.

15 Claims, 13 Drawing Sheets

Specification includes a Sequence Listing.

(56) References Cited

OTHER PUBLICATIONS

Papapetridis et al., "Improving ethanol yield in acetate-reducing *Saccharomyces cerevisiae* by cofactor engineering of 6-phosphogluconate dehydrogenase and deletion of ALD6". Microbial Cell Factories, 2016, pp. 1-16, vol. 15:67.
Papapetridis et al., "Metabolic engineering strategies for optimizing acetate reduction, ethanol yield and osmotolerance in *Saccharomyces cerevisiae*". Biotechnology Biofuels, 2017, pp. 1-14, vol. 10:107.
Yokobori et al., "Birth of Archaeal Cells: Molecular Phylogenetic Analyses of G1P Dehydrogenase, G3P Dehydrogenases, and Glycerol Kinase Suggest Derived Features of Archaeal Membranes Having G1P Polar Lipids". Archaea, 2016, pp. 1-16, vol. 2016.
Zhang et al., "Engineering of the glycerol decomposition pathway and cofactor regulation in an industrial yeast improves ethanol production". Microbiol Biotechnol, 2013, pp. 1153-1160, vol. 40.

* cited by examiner

SEQUENCE LISTING

```
<160> NUMBER OF SEQ ID NOS: 39

<210> SEQ ID NO 1
<211> LENGTH: 335
<212> TYPE: PRT
<213> ORGANISM: Archaeoglobus fulgidus
<220> FEATURE:
<221> NAME/KEY: MISC_FEATURE
<222> LOCATION: (1)..(335)
<223> OTHER INFORMATION: Archaeoglobus fulgidus gpsA

<400> SEQUENCE: 1

Met Ile Val Ser Ile Leu Gly Ala Gly Ala Met Gly Ser Ala Leu Ser
1               5                   10                  15

Val Pro Leu Val Asp Asn Gly Asn Glu Val Arg Ile Trp Gly Thr Glu
            20                  25                  30

Phe Asp Thr Glu Ile Leu Lys Ser Ile Ser Ala Gly Arg Glu His Pro
        35                  40                  45

Arg Leu Gly Val Lys Leu Asn Gly Val Glu Ile Phe Trp Pro Glu Gln
    50                  55                  60

Leu Glu Lys Cys Leu Glu Asn Ala Glu Val Val Leu Leu Gly Val Ser
65                  70                  75                  80

Thr Asp Gly Val Leu Pro Val Met Ser Arg Ile Leu Pro Tyr Leu Lys
                85                  90                  95

Asp Gln Tyr Ile Val Leu Ile Ser Lys Gly Leu Ile Asp Phe Asp Asn
            100                 105                 110

Ser Val Leu Thr Val Pro Glu Ala Val Trp Arg Leu Lys His Asp Leu
        115                 120                 125

Arg Glu Arg Thr Val Ala Ile Thr Gly Pro Ala Ile Ala Arg Glu Val
    130                 135                 140

Ala Lys Arg Met Pro Thr Thr Val Val Phe Ser Ser Pro Ser Glu Ser
145                 150                 155                 160

Ser Ala Asn Lys Met Lys Glu Ile Phe Glu Thr Glu Tyr Phe Gly Val
                165                 170                 175

Glu Val Thr Thr Asp Ile Ile Gly Thr Glu Ile Thr Ser Ala Leu Lys
            180                 185                 190

Asn Val Tyr Ser Ile Ala Ile Ala Trp Ile Arg Gly Tyr Glu Ser Arg
        195                 200                 205

Lys Asn Val Glu Met Ser Asn Ala Lys Gly Val Ile Ala Thr Arg Ala
    210                 215                 220

Ile Asn Glu Met Ala Glu Leu Ile Glu Ile Leu Gly Gly Asp Arg Glu
225                 230                 235                 240

Thr Ala Phe Gly Leu Ser Gly Phe Gly Asp Leu Ile Ala Thr Phe Arg
                245                 250                 255

Gly Gly Arg Asn Gly Met Leu Gly Glu Leu Leu Gly Lys Gly Leu Ser
```

```
            260                 265                 270
Ile Asp Glu Ala Met Glu Leu Glu Arg Gly Val Gly Val Val
        275                 280                 285

Glu Gly Tyr Lys Thr Ala Glu Lys Ala Tyr Arg Leu Ser Ser Lys Ile
        290                 295                 300

Asn Ala Asp Thr Lys Leu Leu Asp Ser Ile Tyr Arg Val Leu Tyr Glu
305                 310                 315                 320

Gly Leu Lys Val Glu Glu Val Leu Phe Glu Leu Ala Thr Phe Lys
                325                 330                 335

<210> SEQ ID NO 2
<211> LENGTH: 467
<212> TYPE: PRT
<213> ORGANISM: Escherichia coli
<220> FEATURE:
<221> NAME/KEY: MISC_FEATURE
<222> LOCATION: (1)..(467)
<223> OTHER INFORMATION: E. coli eutE

<400> SEQUENCE: 2

Met Asn Gln Gln Asp Ile Glu Gln Val Val Lys Ala Val Leu Leu Lys
1               5                   10                  15

Met Gln Ser Ser Asp Thr Pro Ser Ala Ala Val His Glu Met Gly Val
            20                  25                  30

Phe Ala Ser Leu Asp Asp Ala Val Ala Ala Lys Val Ala Gln Gln
        35                  40                  45

Gly Leu Lys Ser Val Ala Met Arg Gln Leu Ala Ile Ala Ala Ile Arg
    50                  55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190

Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285
```

```
Met Glu Gly Gln His Ala Val Lys Leu Thr Ala Glu Gln Ala Gln Gln
        290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
        355                 360                 365

Pro Val Val Arg Val Ala Asn Val Ala Asp Ala Ile Ala Leu Ala Val
370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
    450                 455                 460

Arg Ile Val
465

<210> SEQ ID NO 3
<211> LENGTH: 891
<212> TYPE: PRT
<213> ORGANISM: Escherichia coli
<220> FEATURE:
<221> NAME/KEY: MISC_FEATURE
<222> LOCATION: (1)..(891)
<223> OTHER INFORMATION: E. coli adhE

<400> SEQUENCE: 3

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Thr Phe Gly
            85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
130                 135                 140

Ala Thr Asn Lys Ala Ala Asp Ile Val Leu Gln Ala Ala Ile Ala Ala
145                 150                 155                 160
```

```
Gly Ala Pro Lys Asp Leu Ile Gly Trp Ile Asp Gln Pro Ser Val Glu
            165                 170                 175
Leu Ser Asn Ala Leu Met His His Pro Asp Ile Asn Leu Ile Leu Ala
        180                 185                 190
Thr Gly Gly Pro Gly Met Val Lys Ala Ala Tyr Ser Ser Gly Lys Pro
            195                 200                 205
Ala Ile Gly Val Gly Ala Gly Asn Thr Pro Val Val Ile Asp Glu Thr
210                 215                 220
Ala Asp Ile Lys Arg Ala Val Ala Ser Val Leu Met Ser Lys Thr Phe
225                 230                 235                 240
Asp Asn Gly Val Ile Cys Ala Ser Glu Gln Ser Val Val Val Asp
            245                 250                 255
Ser Val Tyr Asp Ala Val Arg Glu Arg Phe Ala Thr His Gly Gly Tyr
            260                 265                 270
Leu Leu Gln Gly Lys Glu Leu Lys Ala Val Gln Asp Val Ile Leu Lys
        275                 280                 285
Asn Gly Ala Leu Asn Ala Ala Ile Val Gly Gln Pro Ala Tyr Lys Ile
        290                 295                 300
Ala Glu Leu Ala Gly Phe Ser Val Pro Glu Asn Thr Lys Ile Leu Ile
305                 310                 315                 320
Gly Glu Val Thr Val Val Asp Glu Ser Glu Pro Phe Ala His Glu Lys
            325                 330                 335
Leu Ser Pro Thr Leu Ala Met Tyr Arg Ala Lys Asp Phe Glu Asp Ala
            340                 345                 350
Val Glu Lys Ala Glu Lys Leu Val Ala Met Gly Gly Ile Gly His Thr
            355                 360                 365
Ser Cys Leu Tyr Thr Asp Gln Asp Asn Gln Pro Ala Arg Val Ser Tyr
        370                 375                 380
Phe Gly Gln Lys Met Lys Thr Ala Arg Ile Leu Ile Asn Thr Pro Ala
385                 390                 395                 400
Ser Gln Gly Gly Ile Gly Asp Leu Tyr Asn Phe Lys Leu Ala Pro Ser
            405                 410                 415
Leu Thr Leu Gly Cys Gly Ser Trp Gly Gly Asn Ser Ile Ser Glu Asn
            420                 425                 430
Val Gly Pro Lys His Leu Ile Asn Lys Lys Thr Val Ala Lys Arg Ala
        435                 440                 445
Glu Asn Met Leu Trp His Lys Leu Pro Lys Ser Ile Tyr Phe Arg Arg
        450                 455                 460
Gly Ser Leu Pro Ile Ala Leu Asp Glu Val Ile Thr Asp Gly His Lys
465                 470                 475                 480
Arg Ala Leu Ile Val Thr Asp Arg Phe Leu Phe Asn Asn Gly Tyr Ala
            485                 490                 495
Asp Gln Ile Thr Ser Val Leu Lys Ala Ala Gly Val Glu Thr Glu Val
            500                 505                 510
Phe Phe Glu Val Glu Ala Asp Pro Thr Leu Ser Ile Val Arg Lys Gly
            515                 520                 525
Ala Glu Leu Ala Asn Ser Phe Lys Pro Asp Val Ile Ile Ala Leu Gly
        530                 535                 540
Gly Gly Ser Pro Met Asp Ala Ala Lys Ile Met Trp Val Met Tyr Glu
545                 550                 555                 560
His Pro Glu Thr His Phe Glu Glu Leu Ala Leu Arg Phe Met Asp Ile
            565                 570                 575
Arg Lys Arg Ile Tyr Lys Phe Pro Lys Met Gly Val Lys Ala Lys Met
```

```
            580                 585                 590
Ile Ala Val Thr Thr Thr Ser Gly Thr Gly Ser Glu Val Thr Pro Phe
                595                 600                 605

Ala Val Val Thr Asp Asp Ala Thr Gly Gln Lys Tyr Pro Leu Ala Asp
        610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
        660                 665                 670

Gly Gln Ala Leu Gln Ala Leu Lys Leu Leu Lys Glu Tyr Leu Pro Ala
    675                 680                 685

Ser Tyr His Glu Gly Ser Lys Asn Pro Val Ala Arg Glu Arg Val His
        690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
        740                 745                 750

Ala Asn Asp Asn Pro Thr Lys Gln Thr Ala Phe Ser Gln Tyr Asp Arg
    755                 760                 765

Pro Gln Ala Arg Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
        820                 825                 830

Ser Glu Asp Ala Phe Asp Gln Cys Thr Gly Ala Asn Pro Arg Tyr
835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 4
<211> LENGTH: 1008
<212> TYPE: DNA
<213> ORGANISM: Artificial Sequence
<220> FEATURE:
<223> OTHER INFORMATION: Archaeoglobus fulgidus gpsA codon-optimized for
      S. cerevisiae

<400> SEQUENCE: 4
atgattgttt ctattttggg tgctggtgct atgggttctg ctttgtctgt tccattggtt      60
gacaacggta acgaagttag aatttggggt accgaattcg acaccgaaat tttgaagtct     120
atttctgctg gtagagaaca cccaagattg ggtgttaagt tgaacggtgt tgaaattttc     180
tggccagaac aattggaaaa agtgttggaa aacgctgaag ttgttttgtt gggtgtttct     240
accgacggtg tttttgccagt tatgtctaga attttgccat acttgaagga ccaatacatt     300
```

```
gttttgattt ctaagggttt gattgacttc gacaactctg ttttgaccgt tccagaagct    360
gtttggagat tgaagcacga cttgagagaa agaaccgttg ctattaccgg tccagctatt    420
gctagagaag ttgctaagag aatgccaacc accgttgttt tctcttctcc atctgaatct    480
tctgctaaca agatgaagga aattttcgaa accgaatact tcggtgttga agttaccacc    540
gacattattg gtaccgaaat tacctctgct ttgaagaacg tttactctat tgctattgct    600
tggattagag gttacgaatc tagaaagaac gttgaaatgt ctaacgctaa gggtgttatt    660
gctaccagag ctattaacga aatggctgaa ttgattgaaa ttttgggtgg tgacagagaa    720
accgctttcg gtttgtctgg tttcggtgac ttgattgcta ccttcagagg tggtagaaac    780
ggtatgttgg gtgaattgtt gggtaagggt ttgtctattg acgaagctat ggaagaattg    840
gaaagaagag gtgttggtgt tgttgaaggt tacaagaccg ctgaaaaggc ttacagattg    900
tcttctaaga ttaacgctga caccaagttg ttggactcta tttacagagt tttgtacgaa    960
ggtttgaagg ttgaagaagt tttgttcgaa ttggctacct tcaagtaa               1008
```

```
<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ccaaatgcga catgagtcac                                                 20

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
acggacctat tgccattg                                                   18

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ttgttcaatg gatgcggttc                                                 20

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tggtcgacag atacaatcct gg                                              22

<210> SEQ ID NO 9
<211> LENGTH: 20
<212> TYPE: DNA
<213> ORGANISM: Artificial Sequence
<220> FEATURE:
```

```
<223> OTHER INFORMATION: Primer

<400> SEQUENCE: 9
atcccgggtg gaaactaaac                                                    20

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
aggcacaagc ctgttctc                                                      18

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tcctcggtag atcaggtcag                                                    20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
acggtgagct ccgtattatc                                                    20

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
gttttagagc tagaaatagc aagttaaaat aag                                     33

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
gatcatttat ctttcactgc ggag                                               24

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tattgacgcc gggcaagagc                                                    20
```

```
<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16
cgaccgagtt gctcttg                                                        17

<210> SEQ ID NO 17
<211> LENGTH: 104
<212> TYPE: DNA
<213> ORGANISM: Artificial Sequence
<220> FEATURE:
<223> OTHER INFORMATION: Primer

<400> SEQUENCE: 17
gtgcgcatgt tcggcgttc gaaacttctc cgcagtgaaa gataaatgat cgggcaagga           60
cgtcgaccat agttttagag ctagaaatag caagttaaaa taag                          104

<210> SEQ ID NO 18
<211> LENGTH: 104
<212> TYPE: DNA
<213> ORGANISM: Artificial Sequence
<220> FEATURE:
<223> OTHER INFORMATION: Primer

<400> SEQUENCE: 18
gtgcgcatgt tcggcgttc gaaacttctc cgcagtgaaa gataaatgat cccaagaatt           60
cccattattc ggttttagag ctagaaatag caagttaaaa taag                          104

<210> SEQ ID NO 19
<211> LENGTH: 120
<212> TYPE: DNA
<213> ORGANISM: Artificial Sequence
<220> FEATURE:
<223> OTHER INFORMATION: Primer

<400> SEQUENCE: 19
gttgataacg gactagcctt attttaactt gctatttcta gctctaaaac gaagaattcc          60
agtggtcaat gatcatttat ctttcactgc ggagaagttt cgaacgccga aacatgcgca         120

<210> SEQ ID NO 20
<211> LENGTH: 120
<212> TYPE: DNA
<213> ORGANISM: Artificial Sequence
<220> FEATURE:
<223> OTHER INFORMATION: Primer

<400> SEQUENCE: 20
gttgataacg gactagcctt attttaactt gctatttcta gctctaaaac aattcagagc          60
tgttagccat gatcatttat ctttcactgc ggagaagttt cgaacgccga aacatgcgca         120

<210> SEQ ID NO 21
<211> LENGTH: 120
<212> TYPE: DNA
<213> ORGANISM: Artificial Sequence
<220> FEATURE:
<223> OTHER INFORMATION: Primer

<400> SEQUENCE: 21
tagaagaaaa aacatcaaga aacatctttta acatacacaa acacatacta tcagaataca        60
```
tgtaccaacc tgcatttctt tccgtcatat acacaaaata ctttcatata aacttacttg    120

<210> SEQ ID NO 22
<211> LENGTH: 120
<212> TYPE: DNA
<213> ORGANISM: Artificial Sequence
<220> FEATURE:
<223> OTHER INFORMATION: Primer

<400> SEQUENCE: 22
caagtaagtt tatatgaaag tattttgtgt atatgacgga agaaatgca ggttggtaca    60 tgtattctga tagtatgtgt tgtgtatgt taaagatgtt tcttgatgtt ttttcttcta    120

<210> SEQ ID NO 23
<211> LENGTH: 79
<212> TYPE: DNA
<213> ORGANISM: Artificial Sequence
<220> FEATURE:
<223> OTHER INFORMATION: Primer

<400> SEQUENCE: 23
tatatttgat gtaaatatct aggaaataca cttgtgtata cttctcgctt ttcttttatt    60
gcaaattaaa ccttcgagc                                                 79

<210> SEQ ID NO 24
<211> LENGTH: 91
<212> TYPE: DNA
<213> ORGANISM: Artificial Sequence
<220> FEATURE:
<223> OTHER INFORMATION: Primer

<400> SEQUENCE: 24
gcatagaaca ttatccgcgg aaacgggtat taggggtgag ggtgaataag gaaagtcagg    60
gaaatcgggc aagctggagc tcagtttatc a                                   91

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
tggtattggc agtttcgtag                                                20

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
gttatgagaa atgacataat gc                                             22

<210> SEQ ID NO 27
<211> LENGTH: 80
<212> TYPE: DNA
<213> ORGANISM: Artificial Sequence
<220> FEATURE:
<223> OTHER INFORMATION: Primer

<400> SEQUENCE: 27
gtattttggt agattcaatt ctctttccct ttccttttcc ttcgctcccc ttccttatca    60

```
cacaggaaac agctatgacc                                                  80

<210> SEQ ID NO 28
<211> LENGTH: 80
<212> TYPE: DNA
<213> ORGANISM: Artificial Sequence
<220> FEATURE:
<223> OTHER INFORMATION: Primer

<400> SEQUENCE: 28
ataactgtag taatgttact agtagtagtt gtagaacttg tgtataatga taaattggtt      60
gccgcaaatt aaagccttcg                                                  80

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cgaacaagtt gtcaaggctg                                                  20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gcatcgacca aaacacaacg                                                  20

<210> SEQ ID NO 31
<211> LENGTH: 90
<212> TYPE: DNA
<213> ORGANISM: Artificial Sequence
<220> FEATURE:
<223> OTHER INFORMATION: Primer

<400> SEQUENCE: 31
gcatagaaca ttatccgcgg aaacgggtat taggggtgag ggtgaataag gaaagtcagg      60
gaaatcgggc gtacaatgcc tggcatgttc                                       90

<210> SEQ ID NO 32
<211> LENGTH: 80
<212> TYPE: DNA
<213> ORGANISM: Artificial Sequence
<220> FEATURE:
<223> OTHER INFORMATION: Primer

<400> SEQUENCE: 32
tatatttgat gtaaatatct aggaaataca cttgtgtata cttctcgctt ttcttttatt      60
ctcgtccagt tgagtctagc                                                  80

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
```

```
acaattcaga gctgttagcc                                               20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
acactgctga accagtcaag                                               20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
caccaccgaa tggaactctg                                               20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ggtgctggtg ctatgggttc                                               20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ggtttcggtg acttgattgc                                               20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gagtccaaca acttggtgtc                                               20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
accggtaata gcaacggttc                                               20
```

YEAST STRAINS FOR ETHANOL PRODUCTION

CROSS-REFERENCE TO RELATED APPLICATIONS

This application is the National Stage entry of International Application No. PCT/EP2017/083242, filed 18 Dec. 2017, which claims priority to European Patent Application No. 16205338.3, filed 20 Dec. 2017 and European Patent Application No. 1715525.3, filed 10 Feb. 2017.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-508000_ST25.txt" created on 11 Jun. 2019, and 23,886 bytes in size) is submitted concurrently with the instant application, and the entire contents of the Sequence Listing are incorporated herein by reference.

BACKGROUND

Field

The invention relates to a recombinant cell suitable for ethanol production, use of this cell for the production of ethanol, butanol, lactic acid, succinic acid, a plastic, an organic acid, a solvent, an animal feed supplement, a pharmaceutical, a vitamin, an amino acid, an enzyme or a chemical feedstock, and a process for preparing fermentation product using said recombinant cell.

Description of Related Art

By functionally replacing fossil-fuel derived compounds, microbial production of chemicals and transport fuels can contribute to a transition to a sustainable, low-carbon global economy. The total industrial production of fuel ethanol, which reached ca. 100 billion liters in 2015, is predicted to increase further. The yeast *Saccharomyces cerevisiae* is the established microbial cell factory for conversion of starch- and sucrose-derived hexose units to ethanol, as it combines a high ethanol yield and productivity with robustness under process conditions. Efforts in yeast strain improvement and process optimization of corn-starch and cane-sugar-based bioethanol production have further improved product yields and productivity. Furthermore, intensive metabolic and evolutionary engineering studies have yielded yeast strains capable of efficiently fermenting the pentose sugars xylose and arabinose, thus paving the way for yeast-based 'second-generation' bioethanol production from lignocellulosic hydrolysates.

In industrial bioethanol production, the carbohydrate feedstock represents the single largest cost factor. Maximizing ethanol yield on sugar is therefore a key requirement, especially in second-generation processes, whose ethanol yields and productivity are generally still lower than those of first-generation processes. Adequate yeast performance in lignocellulosic hydrolysates also requires tolerance to inhibitors that are released during biomass pre-treatment and hydrolysis. Under anaerobic conditions, wild-type *S. cerevisiae* strains require glycerol formation to re-oxidize NADH formed during biosynthesis or during production of metabolites that are more oxidized than glucose. As the major compatible solute in *S. cerevisiae*, glycerol also plays a key role in osmotolerance.

SUMMARY

It is an object of the invention to provide a novel recombinant cell, which is suitable for the anaerobic, fermentative production of ethanol from a carbohydrate, which has a reduced glycerol production compared to its corresponding wild-type organism or which lacks glycerol production if the cell is used for the fermentative preparation of ethanol.

It is further an object to provide a novel method for fermentatively preparing ethanol in anaerobic yeast cultures, in which method no glycerol is formed or at least wherein less glycerol is formed than in a method making use of known strains of *S. cerevisiae*.

One or more further objects that may be met are apparent from the description and/or claims.

DETAILED DESCRIPTION

Figure 1:
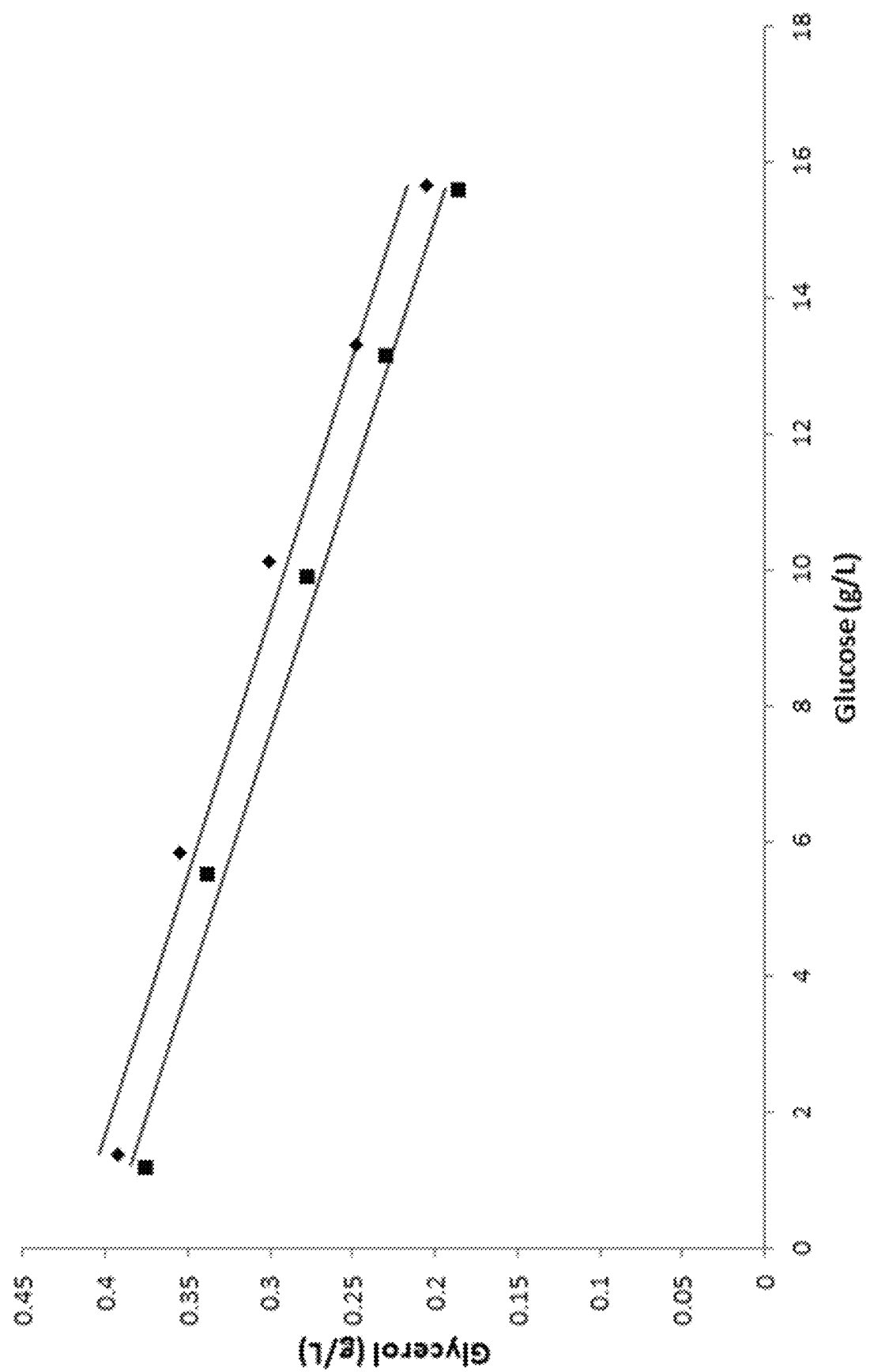
FIG. 1. Calculation of glycerol yield on glucose. Plot displays glycerol versus glucose concentration. Diamonds: IMX884-I. Squares: IMX884-II.
Figure 2:
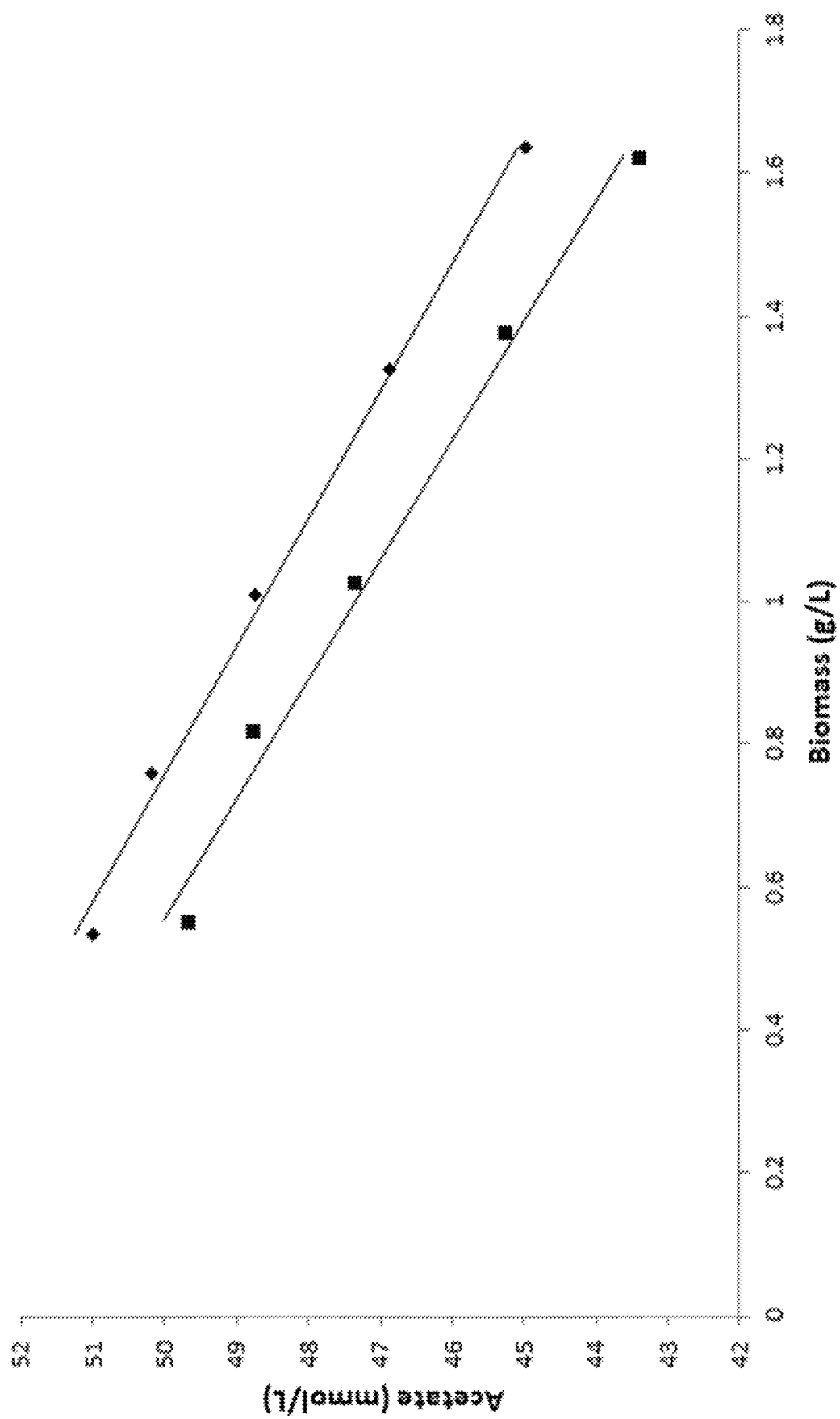
FIG. 2. Calculation of acetate consumption ratio on biomass. Plot displays acetate versus biomass concentration. Diamonds: IMX884-I. Squares: IMX884-II.
Figure 3:
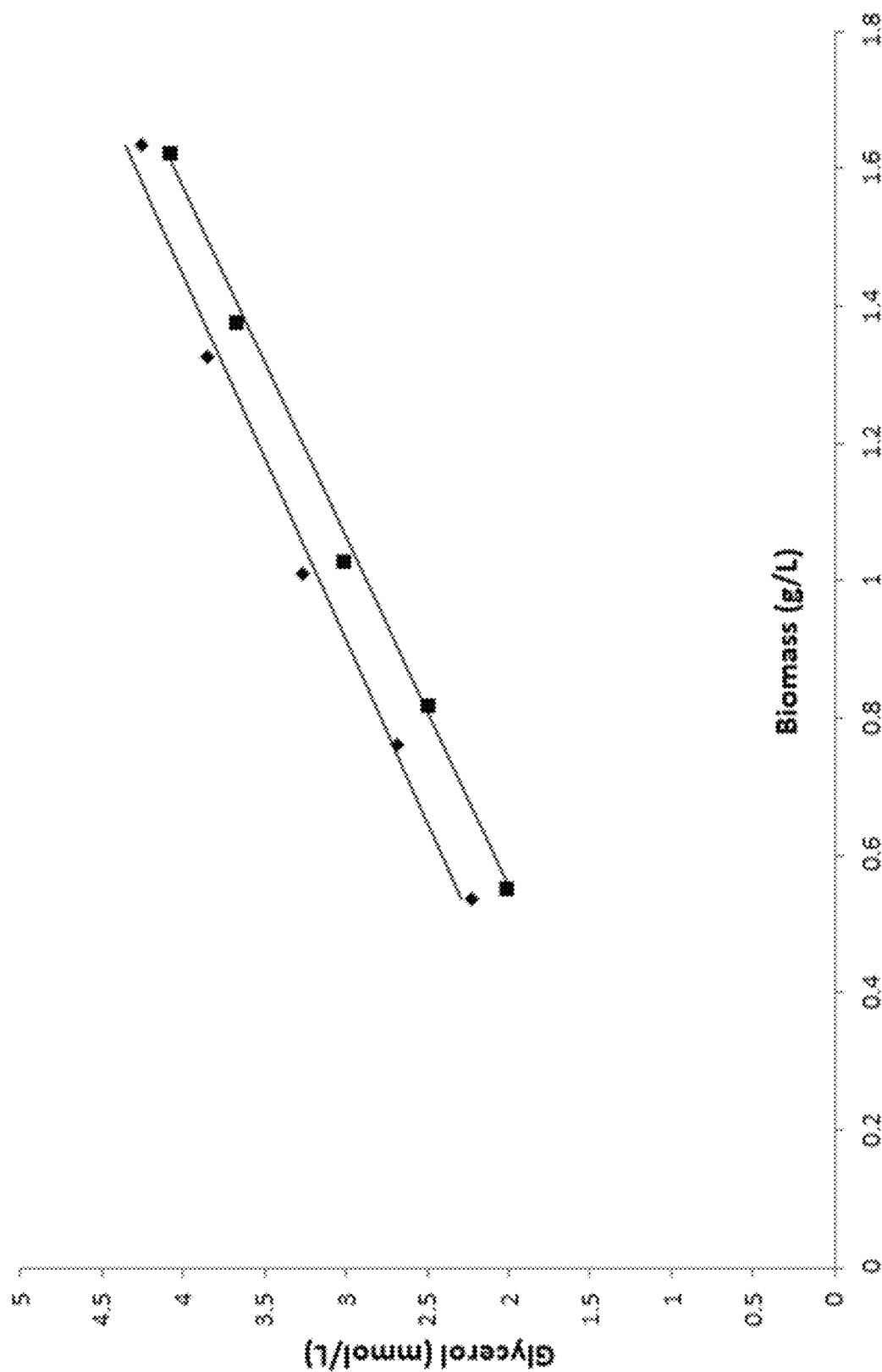
FIG. 3. Calculation of glycerol yield on biomass. Plot displays glycerol versus biomass concentration. Diamonds: IMX884-I. Squares: IMX884-II.
Figure 4:
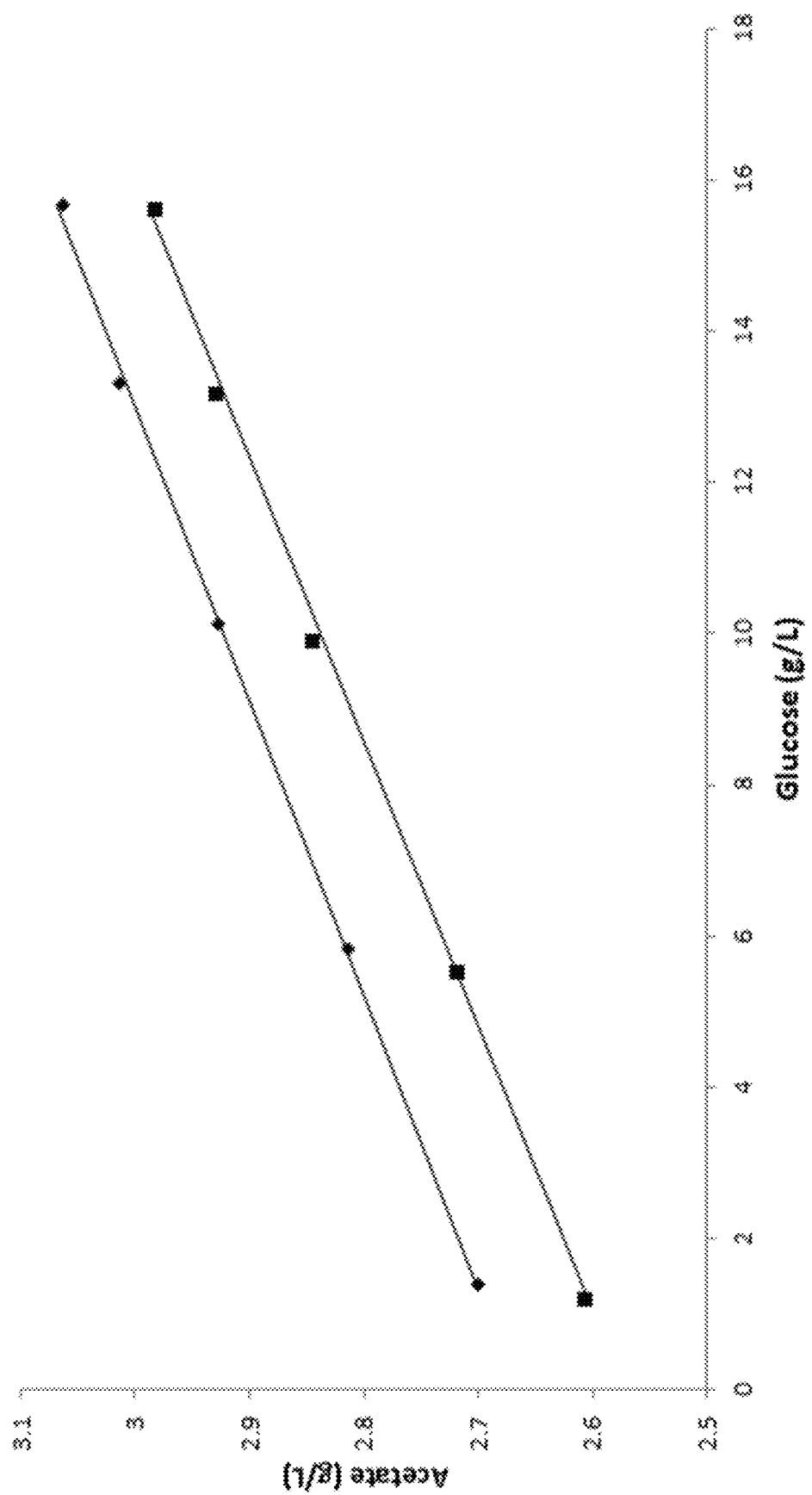
FIG. 4. Calculation of acetate consumption ratio on glucose. Plot displays acetate versus glucose concentration. Diamonds: IMX884-I. Squares: IMX884-II.

The term "a" or "an" as used herein is defined as "at least one" unless specified otherwise.

When referring to a noun (e.g. a compound, an additive, etc.) in the singular, the plural is meant to be included. Thus, when referring to a specific moiety, e.g. "gene", this means "at least one" of that gene, e.g. "at least one gene", unless specified otherwise. The term 'or' as used herein is to be understood as 'and/or'.

When referring to a compound of which several isomers exist (e.g. a D and an L enantiomer), the compound in principle includes all enantiomers, diastereomers and cis/trans isomers of that compound that may be used in the particular method of the invention; in particular when referring to such as compound, it includes the natural isomer(s).

The term 'fermentation', 'fermentative' and the like is used herein in a classical sense, i.e. to indicate that a process is or has been carried out under anaerobic conditions. Anaerobic conditions are herein defined as conditions without any oxygen or in which essentially no oxygen is consumed by the yeast cell, in particular a yeast cell, and usually corresponds to an oxygen consumption of less than 5 mmol/l.h, in particular to an oxygen consumption of less than 2.5 mmol/l.h, or less than 1 mmol/l.h. More preferably 0 mmol/L/h is consumed (i.e. oxygen consumption is not detectable. This usually corresponds to a dissolved oxygen concentration in the culture broth of less than 5% of air saturation, in particular to a dissolved oxygen concentration of less than 1% of air saturation, or less than 0.2% of air saturation.

The term "cell" refers to a eukaryotic or prokaryotic organism, preferably occuring as a single cell. The cell may be selected from the group of fungi, yeasts, euglenoids, archaea and bacteria.

The cell may in particular be selected from the group of genera consisting of yeast.

The term "yeast" or "yeast cell" refers to a phylogenetically diverse group of single-celled fungi, most of which are in the division of Ascomycota and Basidiomycota. The budding yeasts ("true yeasts") are classified in the order Saccharomycetales, with Saccharomyces cerevisiae as the most well-known species.

The term "recombinant (cell)" or "recombinant microorganism" as used herein, refers to a strain (cell) containing nucleic acid which is the result of one or more genetic modifications using recombinant DNA technique(s) and/or another mutagenic technique(s). In particular a recombinant cell may comprise nucleic acid not present in a corresponding wild-type cell, which nucleic acid has been introduced into that strain (cell) using recombinant DNA techniques (a transgenic cell), or which nucleic acid not present in said wild-type is the result of one or more mutations—for example using recombinant DNA techniques or another mutagenesis technique such as UV-irradiation—in a nucleic acid sequence present in said wild-type (such as a gene encoding a wild-type polypeptide) or wherein the nucleic acid sequence of a gene has been modified to target the polypeptide product (encoding it) towards another cellular compartment. Further, the term "recombinant (cell)" in particular relates to a strain (cell) from which DNA sequences have been removed using recombinant DNA techniques.

The term "transgenic (yeast) cell" as used herein, refers to a strain (cell) containing nucleic acid not naturally occurring in that strain (cell) and which has been introduced into that strain (cell) using recombinant DNA techniques, i.e. a recombinant cell).

The term "mutated" as used herein regarding proteins or polypeptides means that at least one amino acid in the wild-type or naturally occurring protein or polypeptide sequence has been replaced with a different amino acid, inserted or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989). The term "mutated" as used herein regarding genes means that at least one nucleotide in the nucleic acid sequence of that gene or a regulatory sequence thereof, has been replaced with a different nucleotide, or has been deleted from the sequence via mutagenesis, resulting in the transcription of a protein sequence with a qualitatively of quantitatively altered function or the knock-out of that gene.

In the context of this invention an "altered gene" has the same meaning as a mutated gene.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e. g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at http://www.chem.qmul.ac.uk/iubmb/enzyme/. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found via www.ncbi.nlm.nih.gov/, (as available on 14 Jun. 2016) unless specified otherwise.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

The term "functional homologue" (or in short "homologue") of a polypeptide having a specific sequence (e.g. SEQ ID NO: X), as used herein, refers to a polypeptide comprising said specific sequence with the proviso that one or more amino acids are substituted, deleted, added, and/or inserted, and which polypeptide has (qualitatively) the same enzymatic functionality for substrate conversion. This functionality may be tested by use of an assay system comprising a recombinant yeast cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity for converting acetyl-Coenzyme A to acetaldehyde in the yeast cell is to be tested, and assessing whether said conversion occurs in said cells. Candidate homologues may be identified by using in silico similarity analyses. A detailed example of such an analysis is described in Example 2 of WO2009/013159. The skilled person will be able to derive there from how suitable candidate homologues may be found and, optionally upon codon (pair) optimization, will be able to test the required functionality of such candidate homologues using a suitable assay system as described above. A suitable homologue represents a polypeptide having an amino acid sequence similar to a specific polypeptide of more than 50%, preferably of 60% or more, in particular of at least 70%, more in particular of at least 80%, at least 90%, at least 95%, at least 97%, at least 98% or at least 99% and having the required enzymatic functionality. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labeled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. In an embodiment, conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. In an embodiment, conservative substitutions for each of the naturally occurring amino acids are as follows: Ala to ser; Arg to lys; Asn to Gln or His; Asp to glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Nucleotide sequences of the invention may also be defined by their capability to hybridise with parts of specific nucleotide sequences disc losed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in eukaryotic host cell systems such as yeast are well known to those of skill in the art. A polynucleotide comprising a nucleic acid sequence of a gene encoding an enzyme with a specific activity can be expressed in such a eukaryotic system. In some embodiments, transformed/transfected yeast cells may be employed as expression systems for the expression of the enzymes. Expression of heterologous proteins in yeast is well known. Sherman, F., et al., Methods in Yeast Genetics, Cold Spring Harbor Laboratory (1982) is a well-recognized work describing the various methods available to express proteins in yeast. Two widely utilized yeasts are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. In an embodiment there is no (external) inducer needed.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleic acid sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

By "host cell" is meant a cell which contains a vector and supports the replication and/or expression of the vector.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

By "disruption" is meant (or includes) all nucleic acid modifications such as nucleotide deletions or substitutions, gene knock-outs, (other) which affect the translation or transcription of the corresponding polypeptide and/or which affect the enzymatic (specific) activity, its substrate specificity, and/or or stability. Such modifications may be targeted on the coding sequence or on the promotor of the gene.

In a first aspect the invention provides a recombinant cell, preferably a recombinant yeast cell, preferably suitable for the production of ethanol, said cell comprising:
 a) a gene coding for an enzyme having glycerol-3-phosphate dehydrogenase activity, wherein said enzyme has a cofactor dependency for at least NADP$^+$ and/or for NADPH;
 b) a gene encoding an enzyme having at least NAD dependent acetylating acetaldehyde dehydrogenase activity (EC 1.2.1.10); and
 c) a mutation or disruption in at least one gene selected from the group of GPD1 and GPD2.

The gene coding for an enzyme having glycerol-3-phosphate dehydrogenase activity, as defined in a), confers to the cell the ability to convert dihydroxyacetone phosphate to glycerol-3-phosphate. *S. cerevisiae* harbours at least two genes encoding a glycerol-3-phosphate dehydrogenase, GPD1 and GPD2. The GPD1 gene is a stress-induced glycerol-3-phosphate dehydrogenase which is important for growth under osmotic stress as may occur under industrial fermentations conditions, e.g. at high glucose concentrations, such as around 180 g/L. The expression of GPD1 is inter alia regulated by the high-osmolarity glycerol response pathway. In one embodiment, therefore, GPD2, but not GDP1 is mutated or disruped. However, the inventors have found that by using an enzyme having glycerol-3-phosphate dehydrogenase activity which enzyme has a cofactor dependency for at least NADP and/or for NADPH, both GPD1 and GPD2 can be mutated or disrupted, whilst the cell is able to grow at high glucose concentrations and produces little or no glycerol. Therefore, in an embodiment, both GPD1 and GPD2 are mutated or disrupted.

In an embodiment the enzyme having glycerol-3-phosphate dehydrogenase activity has a lower Michaelis constant (Km, expressed as M) for NADPH than for NADH. The $Km_{(NADPH)}$ of the enzyme having glycerol-3-phosphate dehydrogenase activity may be at most half of the $Km_{(NADH)}$, preferably the $Km_{(NADPH)}$ of the enzyme having glycerol-3-phosphate dehydrogenase activity is at most one-fourth as compared to the $Km_{(NADH)}$, more preferably at most one-tenth, even more preferably at most 1/20, at most 1/50, even more preferably at most 1/100, at most 1/500, even more preferably at most 1/000 as compared for the $Km_{(NADH)}$.

In another embodiment the enzyme having glycerol-3-phosphate dehydrogenase activity has a higher maximum specific activity (Vmax, expressed as µmol mg/protein/min) for NADPH than for NADH.

The Vmax of the enzyme having glycerol-3-phosphate dehydrogenase activity with NADPH may be at least twice as high as with NADH, preferably the $Vmax_{(NADPH)}$ of the enzyme having glycerol-3-phosphate dehydrogenase activity is at least fourfold, more preferably at least 10 fold, at least 50 fold, at least 100 fold, more preferably at least 500 fold, even more preferably at least 1000 fold as compared to its $Vmax_{(NADH)}$.

The Vmax of the enzyme having glycerol-3-phosphate dehydrogenase activity may refer to the enzyme proper, e.g. in isolated or pure or purified form. The skilled art knows how to purify or isolate glycerol-3-phosphate dehydrogenase. Alternatively, the Vmax of the enzyme having glycerol-3-phosphate dehydrogenase activity may relate vis-a-vis the total amount of protein on the cell, or vis-a-vis the total amount of protein in a free extract of the cell. That is, the Vmax of the enzyme having glycerol-3-phosphate dehydrogenase activity may be determined using whole cells or a cell-free extract.

In another embodiment the enzyme having glycerol-3-phosphate dehydrogenase activity has a lower Michaelis constant and a higher Vmax for NADPH than for NADH.

In yet another embodiment the enzyme having glycerol-3-phosphate dehydrogenase activity has a higher affinity (Vmax/Km) for NADPH than for NADH. The $Vmax/Km_{(NADPH)}$ of the enzyme having glycerol-3-phosphate dehydrogenase activity may be at least twice as compared to its $Vmax/Km_{(NADH)}$, preferably the $Vmax/Km_{(NADPH)}$ of the enzyme having glycerol-3-phosphate dehydrogenase activity is at least four-fold, more preferably at least 10 fold, at least 50 fold, at least 100 fold, more preferably at least 500 fold, even more preferably at least 1000 fold as compared to its $Vmax/Km_{(NADH)}$. The affinity of the enzyme having glycerol-3-phosphate dehydrogenase activity may refer to the enzyme proper, e.g. the enzyme in isolated or pure or purified form. The skilled art knows how to purify or isolate glycerol-3-phosphate dehydrogenase. Alternatively, the affinity of the enzyme having glycerol-3-phosphate dehydrogenase activity may relate vis-a-vis the total amount of protein of the cell, or vis-a-vis the total amount of protein in a free extract of the cell. That is, the affinity of the enzyme having glycerol-3-phosphate dehydrogenase activity may be determined using whole cells or a cell-free extract.

In an embodiment the cell according to the invention is free, or essentially free of, or has reduced NADH-dependent glycerol-3-phosphate dehydrogenase activity compared to its corresponding wildtype cell. Preferably the cell is free, or essentially free of, or has reduced native (endogenous) NADH-dependent glycerol-3-phosphate dehydrogenase activity compared to its corresponding wildtype cell. To compare the activity of the cell of the invention and the wild type cell it is preferred that these activities are measured under the same conditions.

In an embodiment the gene coding for an enzyme having glycerol-3-phosphate dehydrogenase activity comprises at least one exogenous gene, which exogenous gene may encode an enzyme with an amino acid sequence according to SEQ ID NO: 1 or a functional homologue thereof having a sequence identity of at least 50%, preferably at least 60%, at least 70%, more preferably at least 80%, at least 90%, even more preferably at least 95%. A preferred such gene is gpsA, e.g. from *Archaeoglobus fulgidus*.

The cell according to the invention may comprise an altered endogenous gene coding for an enzyme having glycerol-3-phosphate dehydrogenase activity, wherein said alteration confers to the enzyme an increased affinity and/or lower Michaelis constant and/or a higher maximum activity for NADPH for NADPH.

The gene encoding an enzyme having at least NAD dependent acetylating acetaldehyde dehydrogenase activity may encode an enzyme with an amino acid sequence according to SEQ ID NO: 2 or a functional homologue thereof having a sequence identity of at least 50%, preferably at least 60%, at least 70%, more preferably at least 80%, at least 90%, even more preferably at least 95%. A preferred such gene is eutE, e.g. from *E. coli*.

The cell according to the invention may be (essentially) free of, or has reduced NADPH-dependent aldehyde reductase activity (EC 1.2.1.4) compared to its corresponding wildtype cell.

The genome of the cell according to the invention may comprise a mutation in ALD6 or a functional homologue thereof having a sequence identity of at least 50% preferably at least 60%, at least 70%, more preferably at least 80%, at least 90%, even more preferably at least 95%. A mutation in ALD6 or functional homologue may prevent or reduce a lag phase in growth.

In an embodiment the enzyme having at least NAD dependent acetylating acetaldehyde dehydrogenase activity catalyses the reversible conversion of acetyl-Coenzyme A to acetaldehyde and the subsequent reversible conversion of acetaldehyde to ethanol, which the enzyme preferably comprises both $NAD_+$ dependent acetylating acetaldehyde dehydrogenase (EC 1.2.1.10) activity and $NAD_+$-dependent alcohol dehydrogenase activity (EC 1.1.1.1).

In an embodiment the gene encoding an enzyme having at least NAD dependent acetylating acetaldehyde dehydrogenase activity encodes an enzyme with an amino acid sequence according to SEQ ID NO: 3 or a functional homologue thereof having a sequence identity of at least 50%, preferably at least 60%, at least 70%, more preferably at least 80%, at least 90%, even more preferably at least 95%. A preferred such gene is adhE, e.g. from *E. coli*.

In an embodiment the cell does not comprise a gene encoding an enzyme having pyruvate formate lyase activity (EC 2.3.1.54). As herein, a pyruvate-formate lyase catalyses at least the following reaction (I):

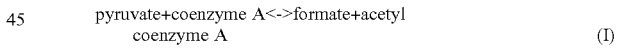

pyruvate+coenzyme A<->formate+acetyl coenzyme A         (I)

The invention also provides the use of a cell according to the invention for the preparation of ethanol, butanol, lactic acid, succinic acid, a plastic, an organic acid, a solvent, an animal feed supplement, a pharmaceutical, a vitamin, an amino acid, an enzyme or a chemical feedstock, preferably ethanol.

The invention further provides a process for preparing fermentation product, comprising preparing a fermentation product from a fermentable carbohydrate, in particular selected from the group of glucose, fructose, sucrose, maltose, xylose, arabinose, galactose and mannose which preparation is carried out under anaerobic conditions using a cell according to the invention. Said fermentable carbohydrate is preferably obtained from starch, cellulose, hemicellulose lignocellulose, and/or pectin. It is understood that the fermentable carbohydrate is a slurry, suspension, or a liquid.

The starch, lignocellulose, and/or pectin may be contacted with an enzyme composition, wherein one or more sugar is produced, and wherein the produced sugar is fermented to give a fermentation product, and wherein the fermentation is conducted with a cell according to the invention.

In an embodiment the fermentable carbohydrate is, or is comprised by a biomass hydrolysate, such as a corn stover or corn fiber hydrolysate. In another embodiment such biomass hydrolysate comprises, or is derived from corn stover and/or corn fiber.

By a "hydrolysate" is meant a polysaccharide-comprising material (such as corn stover, corn starch, corn fiber, or lignocellulosic material, which polysaccharides have been depolymerized through the addition of water to form mono and oligosaccharide sugars. Hydrolysates may be produced by enzymatic or acid hydrolysis of the polysaccharide-containing material.

A biomass hydrolysate may be a lignocellulosic biomass hydrolysate. Lignocellulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof. Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. In addition, pectins and other pectic substances such as arabinans may make up considerably proportion of the dry mass of typically cell walls from non-woody plant tissues (about a quarter to half of dry mass may be pectins). Lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

The fermentation product in the process of the invention may be one or more of ethanol, butanol, lactic acid, succinic acid, a plastic, an organic acid, a solvent, an animal feed supplement, a pharmaceutical, a vitamin, an amino acid, an enzyme or a chemical feedstock.

In an embodiment, the concentration of glucose is 80 g/L or more relative to the volume of the fermentable carbohydrate. This is to say that the initial concentration of glucose, that is, at the start of the fermentation, is preferably 80 g/L or more, preferably 90 g/L or more, 100 g/L or more, 110 g/L or more, 120 g/L or more, 130 g/L or more, 140 g/L or more, 150 g/L or more, 160 g/L or more, 170 g/L or more, 180 g/L or more. The start of the fermentation may be the moment when the fermentable fermentable carbohydrate is brought into contact with the recombinant cell of the invention.

EXAMPLES

Methodology Examples

General Molecular Biology Techniques

Unless indicated otherwise, the methods used are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Strain Propagation and Maintenance

All S. cerevisiae strains used in this example belong to the CEN.PK lineage (Entian and Kötter, 2007) (Table 1). S. cerevisiae cultures were propagated in synthetic medium (Verduyn et al., 1992) containing 20 g/L glucose. E. coli DH5a cultures for plasmid cloning were propagated in LB medium (10 g/L Bacto tryptone, 5 g/L Bacto yeast extract, 5 g/L NaCl) containing 100 mg/L ampicillin. All strains were stored at −80° C., after addition of sterile glycerol (30% v/v) to growing cultures.

TABLE 1

S. cerevisiae strains

| Strain name | Relevant Genotype | Origin |
|---|---|---|
| IMX585 | MAL2-8c SUC2 can1::cas9-natNT2 | Mans et al., 2015 |
| IMX581 | ura3-52 MAL2-8c SUC2 can1::cas9-natNT2 | Mans et al., 2015 |
| IME324 | ura3-52 MAL2-8c SUC2 can1::cas9-natNT2 p426-TEF (empty) | This work |
| IMX884 | ura3-52 MAL2-8c SUC2 can1::cas9-natNT2 gpd2::eutE pROS10-GPD2 | This work |
| IMX992 | ura3-52 MAL2-8c SUC2 can1::cas9-natNT2 sga1::eutE pUDR119 | This work |
| IMX776 | ura3-52 MAL2-8c SUC2 can1::cas9-natNT2 gpd1::gpsA gpd2::eutE pUDR240 | This work |
| IMX901 | ura3-52 MAL2-8c SUC2 can1::cas9-natNT2 gpd1::gpsA gpd2::eutE ald6Δ pUDR240 | This work |
| IMX888 | MAL2-8c SUC2 can1::cas9-natNT2 gpd1Δ gpd2::eutE | Papapetridis et al., 2016 |

TABLE 2

Plasmids

| Plasmid | Characteristics | Origin |
| --- | --- | --- |
| p426-TEF (empty) | 2μ, URA3, TEF1p-CYC1t | Mumberg et al., 1995 |
| pMEL10 | 2μ, KlURA3, SNR52p-gRNA.CAN1.Y-SUP4t | Mans et al., 2015 |
| pMEL11 | 2μ, amdS, SNR52p-gRNA.CAN1.Y-SUP4t | Mans et al., 2015 |
| pROS10 | KlURA3-gRNA.CAN1-2mu-gRNA.ADE2 | Mans et al., 2015 |
| pUDI076 | pRS406-TDH3p-eutE-CYC1t | Papapetridis et al., 2016 |
| pUDR103 | 2μ, KlURA3, SNR52p-gRNA.SGA1.Y-SUP4t | This work |
| pUDR119 | 2μ, amdS, SNR52p-gRNA.SGA1.Y-SUP4t | van Rossum et al., 2016 |
| pUDR240 | KlURA3-gRNA.GPD1-2mu-gRNA.GPD2 | This work |
| pUDR264 | 2μ, amdS, SNR52p-gRNA.ALD6.Y-SUP4t | This work |
| pMK-RQ-gpsA | Delivery vector, codon-optimized gpsA ORF | GeneArt, Germany |

Construction of Expression Cassettes and Plasmids

Plasmids used in this example are listed in Table 2. Plasmids expressing chimeric gRNAs were used for CRISPR/Cas9-mediated genome editing (Mans et al., 2015). Unique Cas9-recognition sequences in GPD1, GPD2, SGA1 and ALD6 were selected as described previously (Papapetridis et al., 2016). PCR for construction of expression cassettes and diagnostic PCR were performed with Phusion Hot Start II High Fidelity DNA Polymerase and Dreamtaq polymerase (Thermo Scientific, Waltham, Mass.), respectively, according to the manufacturer's guidelines. For construction of pUDR240, the backbone of the plasmid was PCR amplified using the double-binding primer 5793 (Table 3) and pROS10 as template. The insert fragment, expressing the GPD1-targeting and GPD2-targeting gRNA cassettes, was amplified using primers 6965-6966 and pROS10 as template. For construction of pUDR103, the plasmid backbone of pMEL10 was PCR amplified using primers 5792-5980. The SGA1-targeting gRNA expression cassette was PCR amplified using primers 5979-7023 and pMEL10 as template. For construction of pUDR264, the plasmid backbone of pMEL11 was PCR amplified using primers 5792-5980. The ALD6-targeting gRNA expression cassette was PCR amplified using primers 5979-7610 and pMEL11 as a template. Plasmids were assembled with the Gibson Assembly Cloning kit (New England Biolabs, Ipswich, Mass.), after downscaling the supplier's protocol to 10 μl reaction volumes. Plasmids pUDR240 and pUDR264 were cloned in E. coli DH5a cells after transformation by electroporation and plasmid re-isolation with a miniprep kit (Sigma-Aldrich, St. Louis, Mo.). Correct clones were verified by restriction digestion or by diagnostic PCR. For single deletion of GPD2, a plasmid backbone was PCR amplified with the double-binding primer 5793 and pROS10 as template. The insert fragment, expressing two identical GPD2-targeting gRNA cassettes, was amplified with primer 6966 and pROS10 as template. For single deletion of GPD2, the two plasmid fragments were transformed directly into yeast cells and assembled in vivo.

An S. cerevisiae codon-optimized version of Archaeglobus fulgidus gpsA (SEQ ID NO: 4), based on the codon preference of highly expressed yeast glycolytic genes (Wiedemann and Boles, 2008), was synthesized by GeneArt GmbH (Regensburg, Germany). An integration cassette for replacing the coding region of GPD1 by the codon-optimized gpsA sequence was PCR amplified with primers 7862-7863 and pMK-RQ-gpsA as template. Codon-optimized expression cassettes for the E. coli EutE acetylating acetaldehyde dehydrogenase gene (TDH3p-eutE-CYC1t), aimed at integration in the GPD2 or SGA1 locus, were amplified with primers 7991-7992 or 7211-7025, respectively, using pUDI076 (Papapetridis et a., 2016) as a template. Integration cassettes were flanked by 60-bp sequences that enabled integration by homologous recombination after CRISPR/Cas9-mediated introduction of double-strand breaks in selected S. cerevisiae genomic loci.

Strain Construction

The lithium acetate/polyethylene glycol method (Gietz and Woods, 2002) was used for yeast transformation. After transformation with plasmids pUDR103, pUDR240 and after single deletion of GPD2, transformants were selected on synthetic medium agar plates (Verduyn et al., 1992) containing 20 g/L glucose. After transformation with plasmids pUDR119 and pUDR264, selection and counter selection were performed as described (Solis-Escalante et al., 2013). Counter selection of plasmids carrying URA3 was performed on YP agar plates (10 g/L Bacto yeast extract, 20 g/L Bacto peptone) supplemented with glucose (20 g/L final concentration) and 5-fluoroorotic acid (1 g/L final concentration). Diagnostic colony PCR was used for genotypic analysis of selected colonies.

Co-transformation of pUDR119 and the SGA/-flanked TDH3p-eutE-CYC1t cassette into strain IMX581 yielded strain IMX992, in which eutE was overexpressed in the presence of functional GPD1 and GPD2 genes.

Co-transformation of the two fragments of the GPD2-targeting gRNA plasmid and the GPD2-flanked TDH3p-eutE-CYC1t cassette to strain IMX581 yielded strain IMX884, in which GPD2 was deleted and eutE was overexpressed.

Co-transformation of pUDR240, the GPD1-flanked gpsA coding sequence and the GPD2-flanked TDH3p-eutE-CYC1t cassette to strain IMX581 yielded strain IMX776, in which gpsA was expressed from the native GPD1 promoter and terminator, GPD2 was deleted and eutE was overexpressed.

Co-transformation of pUDR264 and the repair oligonucleotides 7608-7609, followed by pUDR264 counter-selection, into strains IMX776 yielded strain IMX901, in which ALD6 was deleted.

The empty-vector reference strain IME324 was obtained by transformation of IMX581 with p426-TEF.

Bioreactor Batch Cultivation

Anaerobic batch cultures were grown in 2-L bioreactors (Applikon, Schiedam, The Netherlands) on synthetic medium (Verduyn et al., 1992) supplemented with acetic acid (3 g/L final concentration). In high-osmolarity cultures of the acetate-consuming strains IMX776 and IMX901, the concentration of acetic acid was re-set to 3 g/L when it reached a value below 1.5 g/L, by addition of glacial acetic acid, to prevent acetic-acid limitation. After autoclaving the mineral salt components of the synthetic medium and acetic acid at 120° C. for 20 min, anaerobic growth media were supplemented with sterile antifoam C (0.2 g/L) (Sigma-Aldrich), ergosterol (10 mg/L), Tween 80 (420 mg/L) and filter-sterilized vitamin solution (Verduyn et al; 1992). Glucose solutions were autoclaved separately at 110° C. for 20 min and added to low and high-osmolarity media at final concentrations of 20 g/L and 180 g/L (1 M), respectively. Shake-flask cultures (100 mL) were inoculated with frozen glycerol stock cultures (1 mL) and grown on synthetic medium supplemented with glucose (20 g/L final concentration). These cultures were used as inocula for 100 mL shake-flask pre-cultures on the same medium, which, upon reaching mid-exponential phase ($OD_{660}$ 4-6), were used to inoculate anaerobic bioreactor cultures, yielding an initial $OD_{660}$ of 0.15-0.2. Anaerobic conditions were maintained by continuously sparging nitrogen gas (<10 ppm oxygen) at a rate of 0.5 L/min. Norprene tubing and Viton O-rings were used to minimize oxygen diffusion into the reactors. In low-osmolarity cultures, the culture pH was automatically controlled at 5.0 by addition of 2 M KOH. In high-osmolarity cultures, a 12.5% v/v $NH_4OH$ solution was used as the titrant to prevent nitrogen limitation. The stirrer speed was set at 800 rpm and temperature was controlled at 30° C. Evaporation was minimized by cooling the outlet gas to 4° C. in a condenser.

Enzyme-Activity Assays

Cell extracts were prepared by sonication (Postma et al., 1989), from exponentially growing shake-flask cultures ($OD_{660}$ 5-6) on synthetic medium containing 20 g/L glucose. Enzyme-activity assays were performed at 30° C. by continuous spectrophotometric monitoring of the conversion of NAD(P)H to $NAD(P)^+$ at 340 nm. For determination of acetylating acetaldehyde dehydrogenase activity, cells were sonicated in 100 mM potassium phosphate buffer (KPB, pH 7.5) with 2 mM $MgCl_2$ and 1 mM dithiothreitol. The 1 mL reaction mixture contained 50 mM KPB (pH 7.5), 0.15 mM NADH and 50 or 70 µL cell extract. Reactions were started by addition of acetyl-CoA to a final concentration of 0.5 mM. For glycerol-3-phosphate dehydrogenase assays, 20 mM Tris-HCl (pH 8.2) buffer supplemented with 10 mM EDTA was used for harvesting and storage of cells and sonication was done in 20 mM Tris-HCl (pH 8.2) buffer with 2 mM EDTA. The 1 mL reaction mixture contained 50 mM Tris-HCl (pH 6.6), 2 mM EDTA, 0.15 mM NADH or NADPH and 50 or 70 µL cell extract. The reaction was started by addition of dihydroxy-acetone phosphate to a final concentration of 4 mM. All assays were performed on samples from two independent cultures and enzyme activities were proportional to the volume of cell extract added to the assay.

Intracellular Glycerol Determination

Shake-flask pre-cultures on synthetic medium (20 g/L glucose) were inoculated from frozen stocks. After reaching mid-exponential phase, cells were washed with sterile demineralized water and used as inoculum for anaerobic shake-flask cultures on the same medium as the high-osmolarity bioreactor batch cultivations. Anaerobic shake-flask cultures were grown in a Bactron anaerobic chamber (Sheldon Manufacturing, Cornelius, Oreg.) at 30° C. Mid-exponential phase cultures were harvested and centrifuged at 4000×g for 5 min. The supernatant was discarded, cells were resuspended in 0.005 mol/L $H_2SO_4$ and incubated at 100° C. for 5 min. The cell suspension was centrifuged at 4000×g for 5 min and the supernatant was used for HPLC analysis. For calculation of the pellet volume, an average density of the pellet of 1.1 g/mL was used (Bryan et al; PNAS. 2010; 107:999-1004). For conversion of intracellular glycerol concentration from g/g dry weight to g/L, an intracellular volume of 2.6 mL (g/dry weight) was used (Albertyn et al., 1994).

Analytical Methods

Biomass dry weight determination, HPLC analysis of extracellular metabolites and correction for ethanol evaporation were performed as previously described (Guadalupe-Medina et al., 2010). Culture offgas composition was analysed as previously described (Guadalupe-Medina et al., 2010), except for batch cultures grown under high-osmolarity conditions with strains IMX992, IMX884, IMX776 and IMX901, in which production of $CO_2$ was calculated from ethanol production, assuming formation of 1 mol $CO_2$ per mol ethanol produced. Prior to glucose and ethanol concentration measurements in high-osmolarity fermentations, culture supernatant was diluted 1:1 with demineralized water. Product yields and ratios in batch cultures were calculated from a minimum of five samples taken during the mid-exponential growth phase (Papapetridis et al., 2016). Biomass concentrations corresponding to samples taken before the mid-exponential growth phase ($OD_{660}<1$) were calculated based on $OD_{660}$ measurements, using calibration curves based on a minimum of five samples taken in mid-exponential phase for which biomass dry weight and $OD_{660}$ were measured (Papapetridis et al., 2016). Examples of calculations can be found in FIGS. 1-4 and 7-8.

TABLE 3

Oligonucleotide primers used for strain construction.

| Primer | SEQ ID |
|---|---|
| 2015 | SEQ ID NO: 5 |
| 2112 | SEQ ID NO: 6 |
| 7298 | SEQ ID NO: 7 |
| 4229 | SEQ ID NO: 8 |
| 2164 | SEQ ID NO: 9 |
| 2171 | SEQ ID NO: 10 |
| 4397 | SEQ ID NO: 11 |
| 4401 | SEQ ID NO: 12 |
| 5792 | SEQ ID NO: 13 |
| 5793 | SEQ ID NO: 14 |
| 5979 | SEQ ID NO: 15 |
| 5980 | SEQ ID NO: 16 |
| 6965 | SEQ ID NO: 17 |
| 6966 | SEQ ID NO: 18 |
| 7023 | SEQ ID NO: 19 |
| 7610 | SEQ ID NO: 20 |
| 7608 | SEQ ID NO: 21 |
| 7609 | SEQ ID NO: 22 |
| 7025 | SEQ ID NO: 23 |
| 7211 | SEQ ID NO: 24 |
| 7862 | SEQ ID NO: 25 |
| 7863 | SEQ ID NO: 26 |
| 7991 | SEQ ID NO: 27 |
| 7992 | SEQ ID NO: 28 |
| 8337 | SEQ ID NO: 29 |
| 8338 | SEQ ID NO: 30 |
| 9809 | SEQ ID NO: 31 |
| 9810 | SEQ ID NO: 32 |

TABLE 3-continued

Oligonucleotide primers used for strain construction.

| Primer | SEQ ID |
|---|---|
| 7678 | SEQ ID NO: 33 |
| 7611 | SEQ ID NO: 34 |
| 7612 | SEQ ID NO: 35 |
| 8034 | SEQ ID NO: 36 |
| 8035 | SEQ ID NO: 37 |
| 8036 | SEQ ID NO: 38 |
| 8037 | SEQ ID NO: 39 |

Example 1

Limited Impact of the Expression of an Acetate-Reduction Pathway in GPD1 GPD2 S. Cerevisiae To investigate the impact of co-expressing an acetate-reduction pathway with a fully functional glycerol pathway, growth and product formation of strain IMX992 (GPD1 GPD2 sga1::eutE) were analysed in anaerobic, glucose-grown bioreactor batch cultures on 20 g/L glucose, supplemented with 3 g/L acetic acid (FIG. 9, Table 4) and compared with the acetate non-reducing reference strain IME324. Under these conditions IME324 (GPD1 GPD2) showed an acetate consumption of 2.43 mmol/(g biomass) (Table 4). Strain IMX992 (GPD1 GPD2sga1::eutE) showed an acetate consumption of 3.35 mmol/(g biomass), which was only 0.92 mmol/(g biomass) higher than the acetate consumption by the GPD1 GPD2 reference strain IME324. Consistent with its marginally higher acetate consumption, glycerol production by strain IMX992 decreased only slightly, from 9.19 to 8.28 mmol glycerol/(g biomass), relative to strain IME324 (Table 4). Clearly, in glucose-fermenting engineered S. cerevisiae strains, EutE-based acetate reduction could not efficiently compete for NADH with a fully functional native glycerol pathway.

Example 2

Deletion of GPD2 Improves Acetate Reduction by an eutE-Expressing Strain

Figure 9:
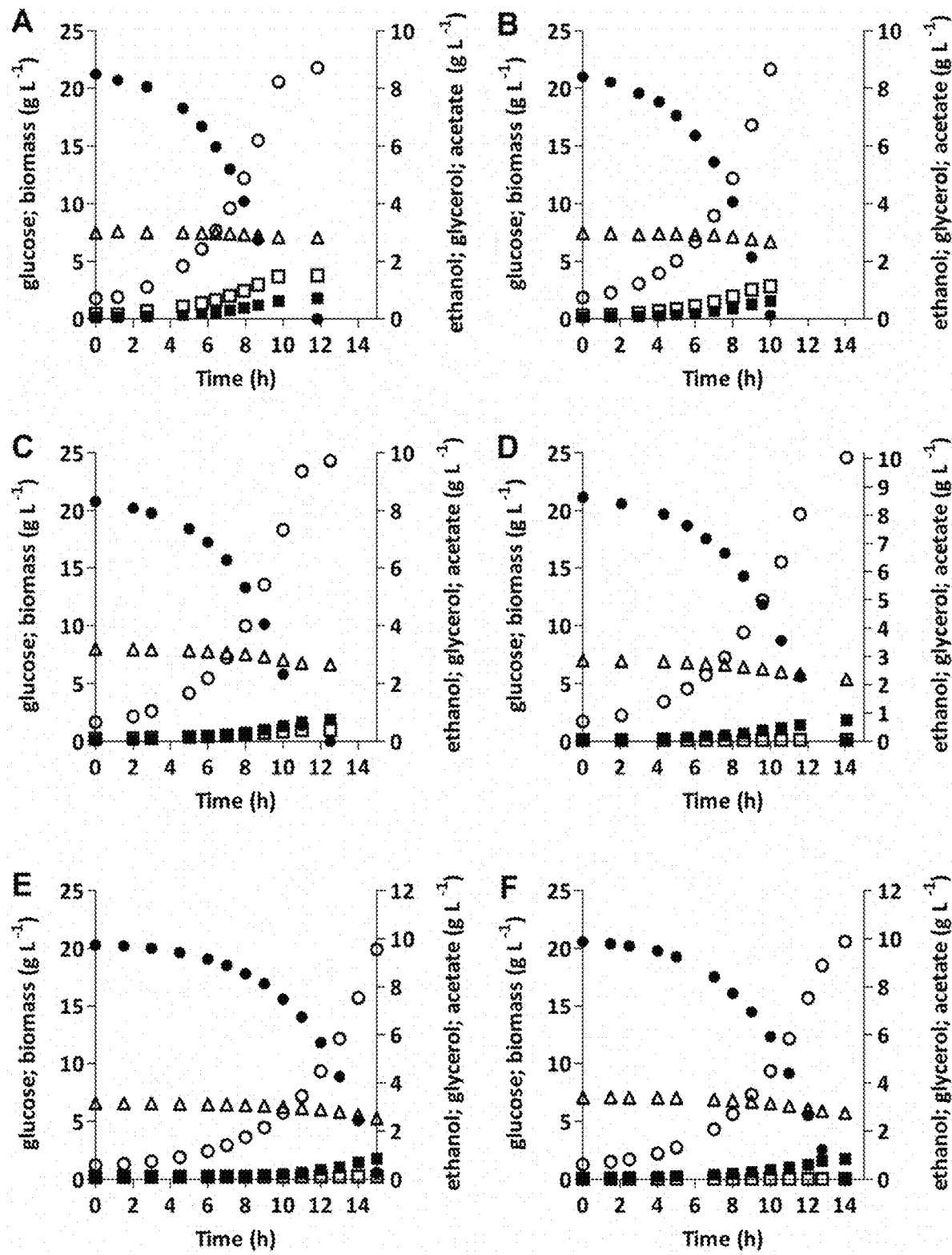
FIG. 9. Growth, glucose consumption and product formation in anaerobic bioreactor batch cultures of *S. cerevisiae* strains with different genetic modifications in glycerol and acetate metabolism. Cultures were grown on synthetic medium containing 20 g/L glucose and 3 g/L acetic acid (pH 5). A, strain IME324 (GPD1 GPD2); B, strain IMX992 (GPD1 GPD2 sga1::eutE); C, strain IMX884 (GPD1 gpd2::eutE); D, strain IMX776 (gpd1::gpsA gpd2::eutE); E, strain IMX901 (gpd1::gpsA gpd2::eutE ald6Δ); F, strain IMX888 (gpd1Δ gpd2::eutE). Symbols: ●, glucose; ■, biomass; □, glycerol; ○, ethanol; Δ, acetate. Panels A-F display single representative cultures from a set of two independent duplicate cultures for each strain. Data on strain IMX888 were taken from (Papapetridis et al., 2016).
Figure 10:
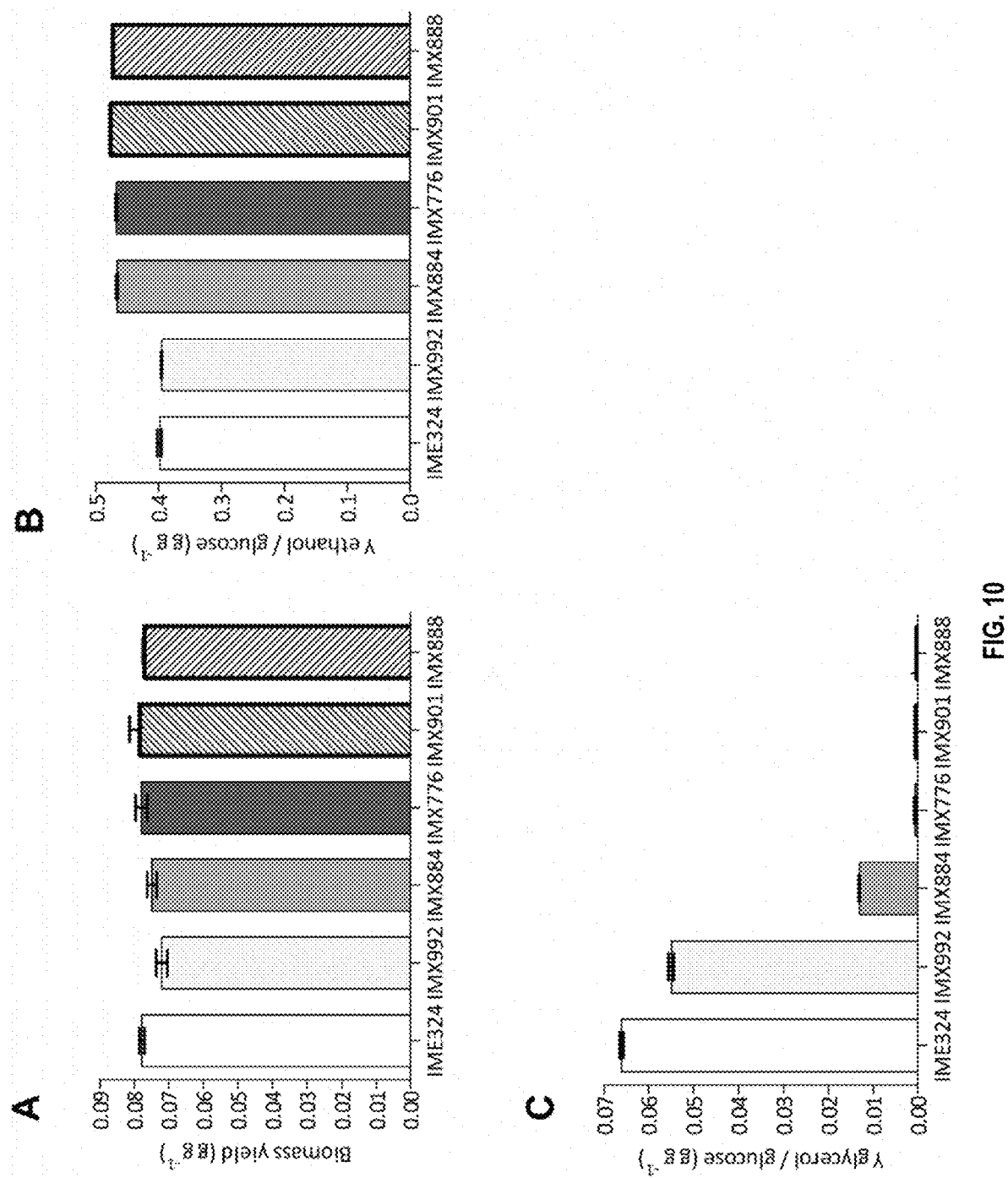
FIG. 10. Biomass and product yields in anaerobic bioreactor batch cultures of S. cerevisiae strains with different genetic modifications in glycerol and acetate metabolism. Cultures were grown on synthetic medium containing 20 g/L glucose and 3 g/L acetic acid (pH 5). Bars refer to the following engineered S. cerevisiae strains: IME324 (GPD1 GPD2); IMX992 (GPD1 GPD2 sga1::eutE); IMX884 (GPD1 gpd2::eutE); IMX776 (gpd1::gpsA gpd2::eutE); IMX901 (gpd1::gpsA gpd2::eutE ald6Δ); IMX888 (gpd1Δ gpd2::eutE). A, biomass yield on glucose; B, ethanol yield on glucose (corrected for ethanol evaporation); C, glycerol yield on glucose. Data represent the averages±mean deviations of measurements on independent duplicate cultures for each strain. Data on strain IMX888 were taken from (Papapetridis et al., 2016).

In acetate-supplemented anaerobic cultures of strain IMX884 (GPD1 gpd2::eutE), eutE expression fully compensated for the absence of a functional Gpd2 enzyme, both in terms of specific growth rate and in terms of biomass yield on glucose (Table 4, FIGS. 9 and 10). Compared to strain IMX992 (GPD1 GPD2 sga1::eutE), strain IMX884 showed a 4-fold lower production of glycerol (1.92 and 8.28 mmol glycerol/(g biomass), respectively) and a correspondingly higher EutE-based acetate consumption (3.34 and 0.92 mmol acetate/(g biomass), respectively, corrected for acetate consumption by the acetate non-reducing reference strain IME324), resulting in an ethanol yield on glucose of 0.46 g/g (FIG. 10). These results indicate that, at least in low-osmolarity media, inactivation of GPD2 enables the EutE-based acetate reduction pathway to efficiently compete for redox equivalents with the glycerol pathway. This engineering strategy not only resulted in a higher acetate consumption, but also in a higher ethanol yield on glucose than observed in the acetate non-reducing reference strain IME324 (Table 4, FIG. 10).

Example 3

Functional Expression of an NADPH-Preferring G3PDH in S. Cerevisiae

As outlined above, expression of the NADP$^+$-preferring G3PDH encoded by A. fulgidus gpsA might enable strategies to uncouple the roles of glycerol metabolism in yeast osmotolerance and redox balancing. To investigate whether gpsA can be functionally expressed in S. cerevisiae, its coding sequence was codon-optimized for expression in yeast (SEQ ID NO: 4) and integrated at the GPD1 locus of strain IMX581 (along with integration of eutE at the GPD2 locus), yielding strain IMX776 (gpd1::gpsA gpd2::eutE). This insertion was designed to place gpsA under the control of the GPD1 promoter and terminator, in order to enable upregulation of its expression at high-osmolarity (Albertyn et al., 1994; Ansell et al., 1997).

Figure 11:
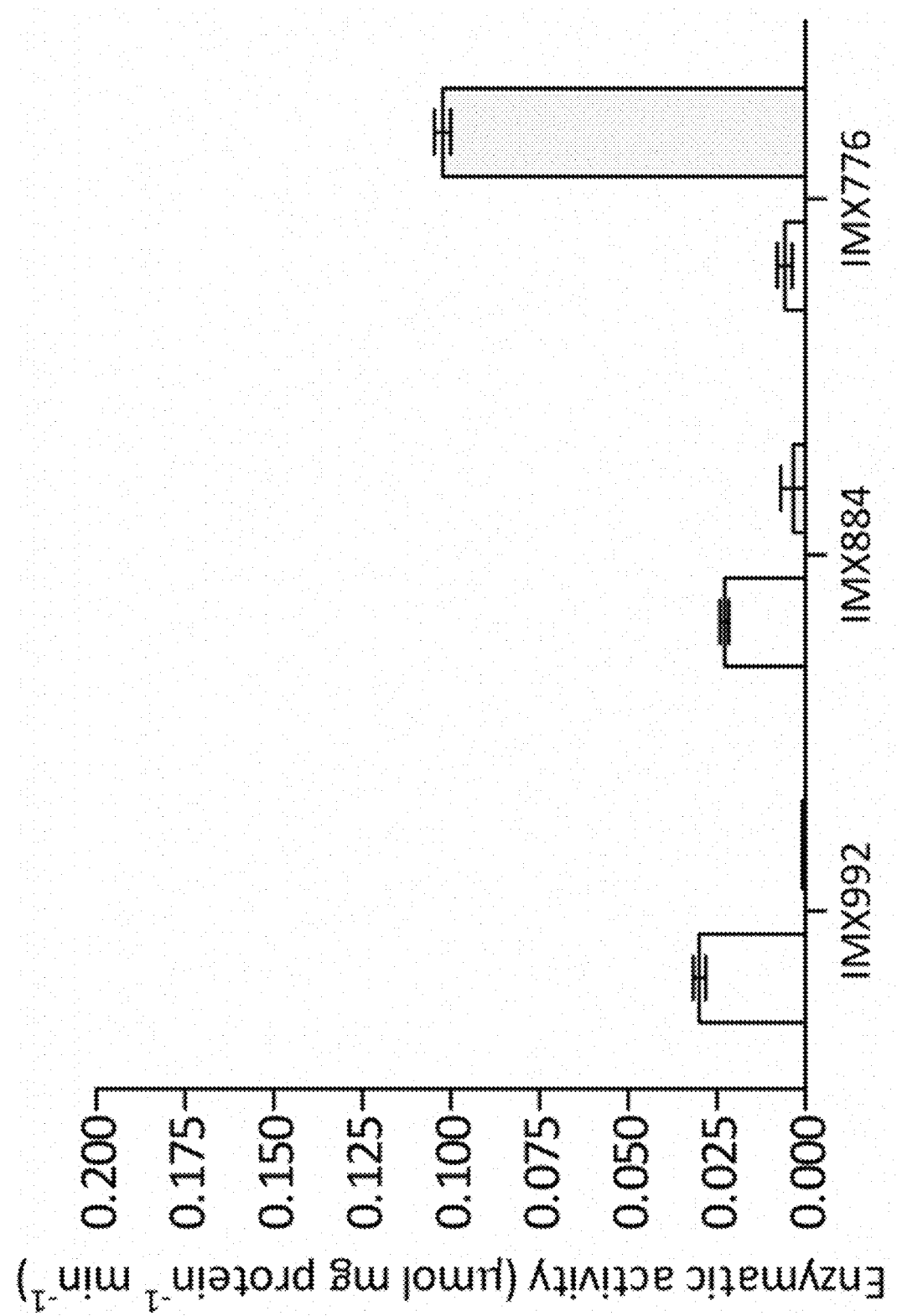
FIG. 11. Specific rates of NADH-dependent (white bars) and NADPH-dependent (gray bars) reduction of dihydroxyacetone phosphate by cell extracts of shake-flask cultures on synthetic medium (20 g/L glucose) of S. cerevisiae strains IMX992 (GPD1 GPD2), IMX884 (GPD1 gpd2::eutE) and IMX776 (gpd1::gpsA gpd2::eutE). Data represent averages±mean deviations of assays on independent duplicate cultures.

Enzyme activity assays in cell extracts showed that, in strain IMX776, replacement of the native GPD1 and GPD2 genes by gpsA resulted in a switch in cofactor preference of glycerol-3-phosphate dehydrogenase (G3PDH, FIG. 11). The gpsA-expressing strain showed in vitro activities of 0.103±0.004 µmol/mg protein/min and 0.006 µmol/mg protein/min with NADPH and NADH, respectively. As a result, the ratio of NADPH– and NADH-linked rates of dihydroxyacetone phosphate reduction was ca. 500-fold higher in strain IMX776 that in the reference strain IMX992, which expresses the native GPD1 and GPD2 genes.

Example 4

Increased Acetate Reduction and Decreased Glycerol Production in a gpsA-Expressing Yeast Strain ALD6 was deleted in the gpsA-expressing, acetate-reducing strain IMX776 (gpd1::gpsA gpd2::eutE), yielding strain IMX901. In anaerobic, acetate-supplemented bioreactor batch cultures the specific growth rate of strain IMX776 (gpd1::gpsA gpd2::eutE) was 0.24/h, which was ca. 20% lower than that of the reference strain IME324 (GPD1 GPD2). The physiology of strain IMX776 in these anaerobic low-osmolarity cultures, including the stoichiometry of biomass formation and acetate consumption, closely resembled that of strain IMX888 (gpd1Δ gpd2::eutE) (Table 4, FIGS. 9 and 10). Virtually no extracellular glycerol was formed in strain IMX776, indicating that, under these conditions, the in vivo activity of NADPH-dependent glycerol production in this strain was minimal. Consistent with this notion, growth and product formation in anaerobic cultures of strain IMX901 (gpd1::gpsA gpd2::eutE ald6Δ was similar to the observed performance of strains IMX776 or IMX888 under these conditions.

Example 5

Growth at High-Osmolarity Negatively Affects Acetate Reduction by a gpd2d Strain To assess the impact of high-osmolarity on the acetate reduction observed in the GPD1 gpd2::eutE strain IMX884, its performance was compared with that of strain IMX992 (GPD1 GPD2 sga1::eutE) in anaerobic bioreactor batch cultures grown on 1 mol/L (180 g/L) glucose. In contrast to the low-osmolarity cultures, in which strains continued to grow exponentially until glucose was depleted (FIG. 9), high-osmolarity conditions showed a biphasic growth profile, in which the exponential phase was followed by second, slower growth phase (FIG. 12).

Figure 12:
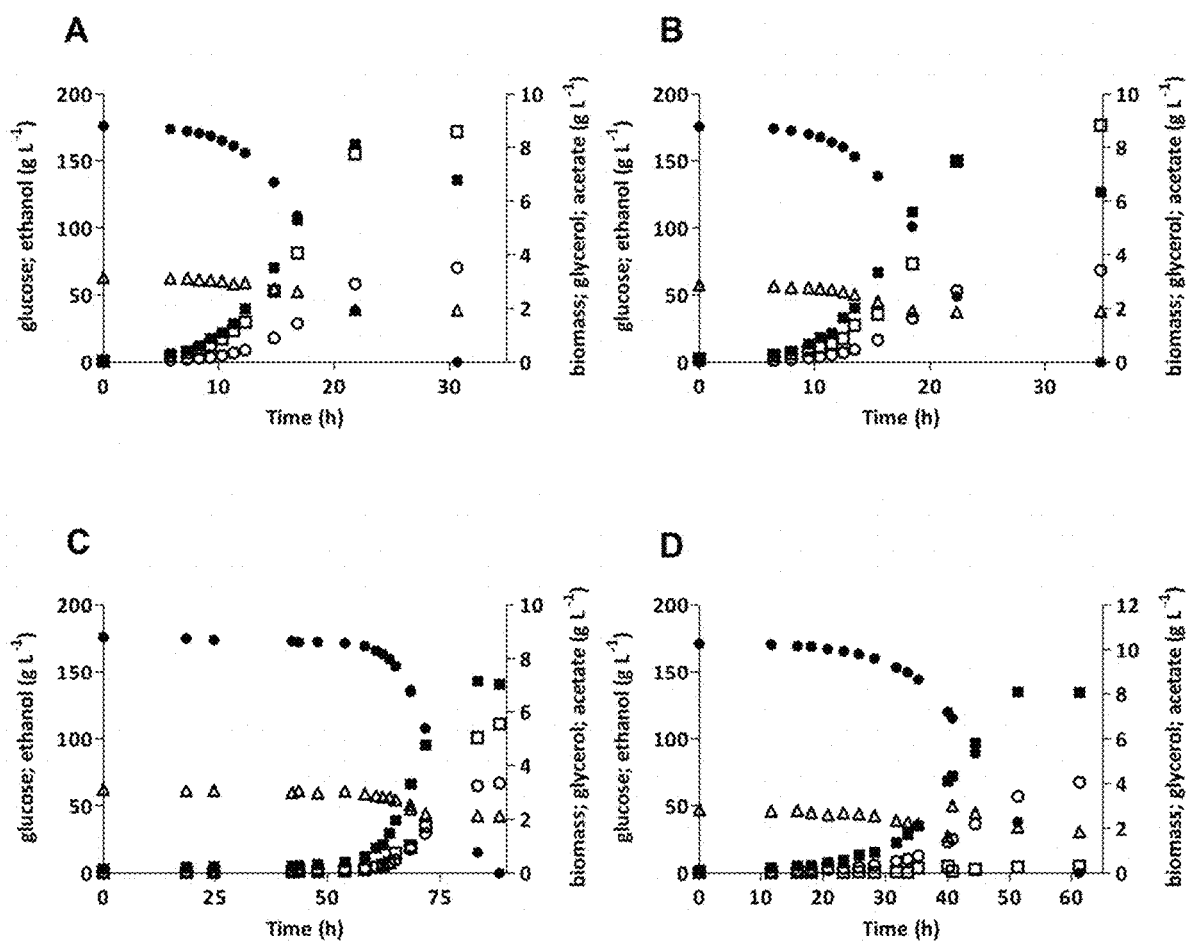
FIG. 12. Growth, glucose consumption and product formation in anaerobic bioreactor batch cultures of S. cerevisiae strains with different genetic modifications in glycerol and acetate metabolism. Cultures were grown on synthetic medium containing 180 g/L glucose and 3 g/L acetic acid (pH 5). A, strain IMX992 (GPD1 GPD2 sga1::eutE); B, strain IMX884 (GPD1 gpd2::eutE); C, strain IMX776 (gpd1::gpsA gpd2::eutE); D, strain IMX901 (gpd1::gpsA gpd2::eutE ald6Δ). Symbols: ●, glucose; ■, biomass; □, glycerol; ○, ethanol; Δ, acetate. Panels A-C display single representative cultures from a set of two independent duplicate cultures for each strain. In the case of IMX901, acetic acid was added externally immediately after the exponential growth phase was finished.

The initial specific growth rate of strain IMX992 (GPD1 GPD2 sga1::eutE) was not affected by increasing the glucose concentration in the medium to 1 mol/L (Tables 4 and 5, FIG. 12). Acetate consumption in the high-osmolarity cultures by this strain was lower than observed during growth on 20 g/L glucose (2.67 and 3.35 mmol/(g biomass), respectively). This observation indicates that, also under high-osmolarity conditions, EutE-mediated acetate reduction could not efficiently compete for NADH with a fully functional glycerol pathway.

Strain IMX884 (GPD1 gpd2::eutE) showed a 10% lower specific growth rate in high-osmolarity medium than in cultures grown on a low glucose concentration (Tables 4 and 5). Relative to its performance in low-osmolarity cultures, growth on 1 mol/L glucose led to a three-fold increase in extracellular glycerol production (6.34 mmol/(g biomass) versus 1.92 mmol/(g biomass)) and a corresponding decrease in acetate consumption (2.98 mmol/$g_x$ versus 5.77 mmol/$g_x$) (Tables 4 and 5). These changes largely eliminated the four-fold difference in glycerol production between strains IMX992 and IMX884 that was observed in low-osmolarity cultures (Tables 4 and 5). After complete glucose consumption, concentrations of acetic acid, glycerol and ethanol reached similar concentrations in high-osmolarity cultures of the two strains (FIG. 12). These results indicate that, even when GPD2 is deleted, high-osmolarity conditions impeded the competition of the EutE-based acetate reduction pathway for NADH with the glycerol pathway, possibly due to osmotic-stress induced upregulation of GPD1.

Example 6

Replacement of GPD1 and GPD2 by gpsA Uncouples the Roles of Glycerol Formation in Redox Metabolism and Osmoregulation To test whether replacement of the yeast $NAD^+$-dependent Gpd isoenzymes by an $NADP^+$-preferring G3PDH can uncouple the roles of glycerol formation in osmoregulation and redox metabolism, growth and product formation of strain IMX776 (gpd1::gpsA gpd2::eutE) was investigated in high-osmolarity cultures. In contrast to strains IMX992 and IMX884, strain IMX776 showed a lag phase of ca. 50 h under these conditions (FIG. 12) and its specific growth rate was 60% lower than in low-osmolarity cultures (Tables 4 and 5). While, under low-osmolarity conditions, this strain did not produce extracellular glycerol, high-osmolarity batch cultures showed a glycerol production of 3.29 mmol/(g biomass) (Table 5). After glucose depletion, the glycerol concentration in high-osmolarity cultures of strain IMX776 was 44% lower than observed for strain IMX992 (GPD1 GPD2 sga1::eutE) (FIG. 12).

Figure 6:
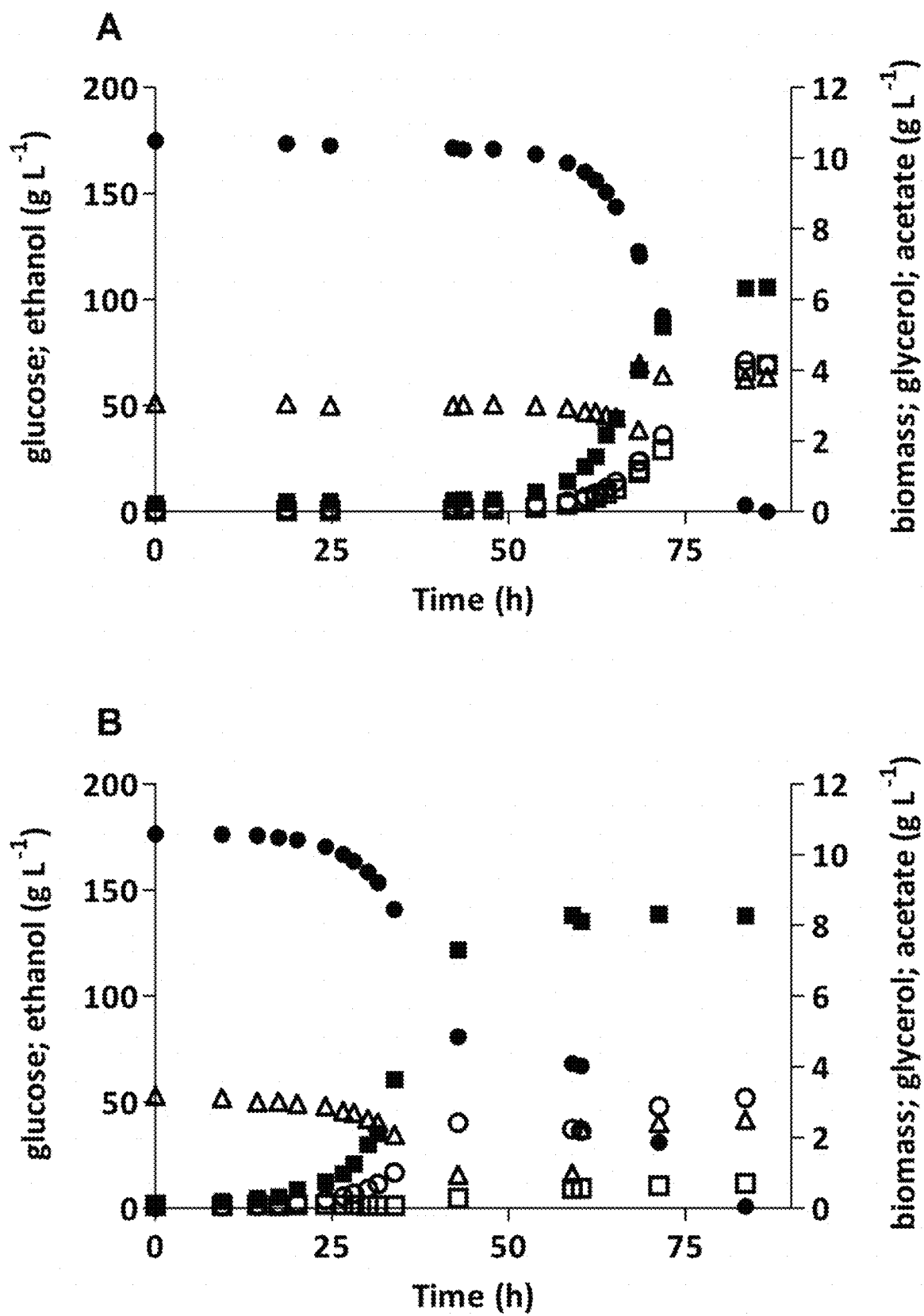
FIG. 6. Growth, glucose consumption and product formation in anaerobic bioreactor batch cultures of *S. cerevisiae* strains with different genetic modifications in glycerol and acetate metabolism. Cultures were grown on synthetic medium containing 180 g/L glucose and 3 g/L acetic acid (pH 5). A, strain IMX776 (gpd1::gpsA gpd2::eutE); B, strain IMX901 (gpd1::gpsA gpd2::eutE ald6Δ). Symbols: ●, glucose; ■, biomass; □, glycerol; ○, ethanol; Δ, acetate. In the case of IMX776, acetic acid was added externally immediately after the exponential growth phase was finished. In the case of IMX901, acetic acid was added externally after 20 h in stationary phase.
Figure 7:
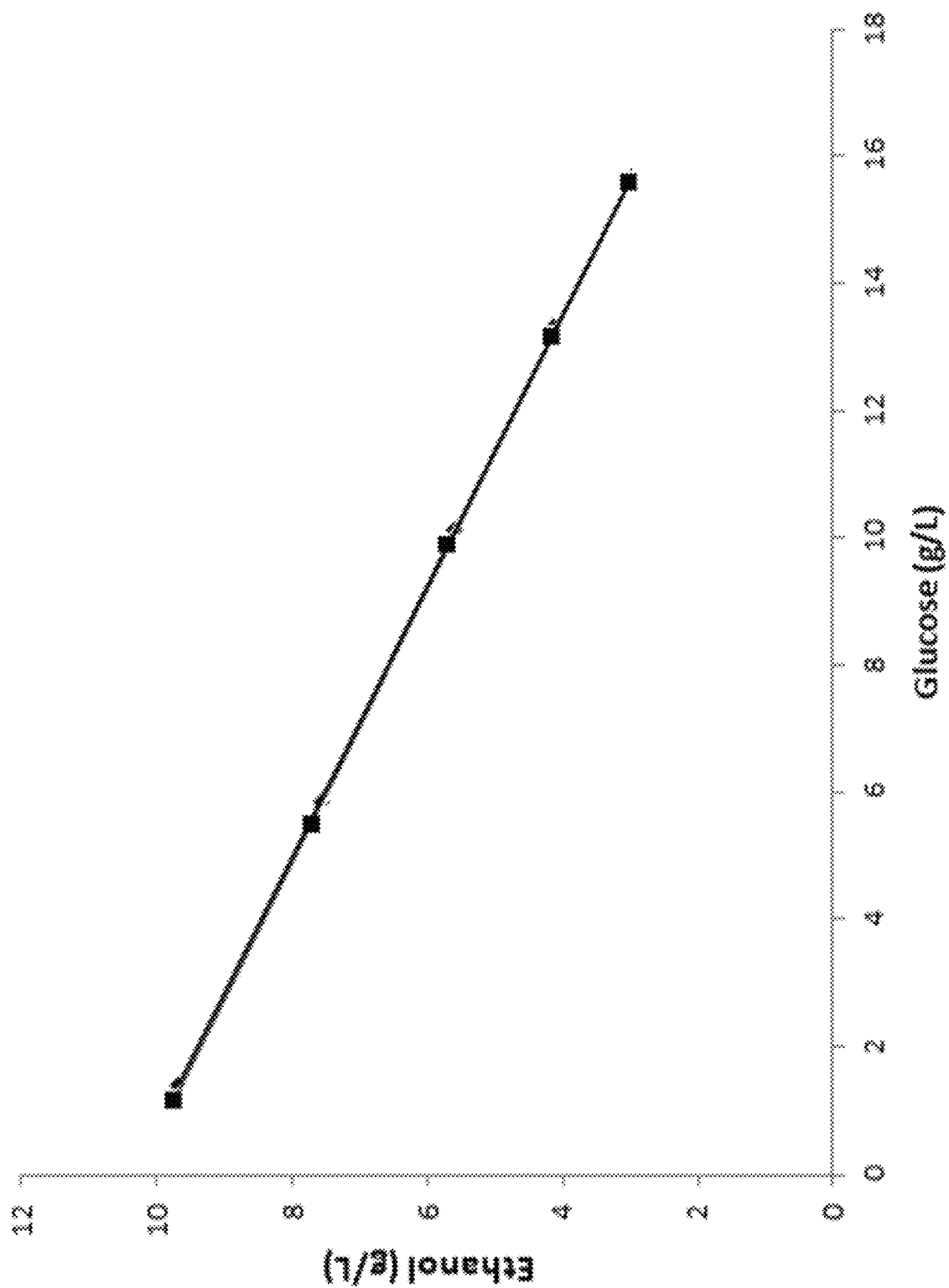
FIG. 7. Calculation of ethanol yield on glucose. Plot displays ethanol versus glucose concentration. Diamonds: IMX884-I. Squares: IMX884-II. The values for IMX884-I are mostly overlapping with IMX884-II.
Figure 8:
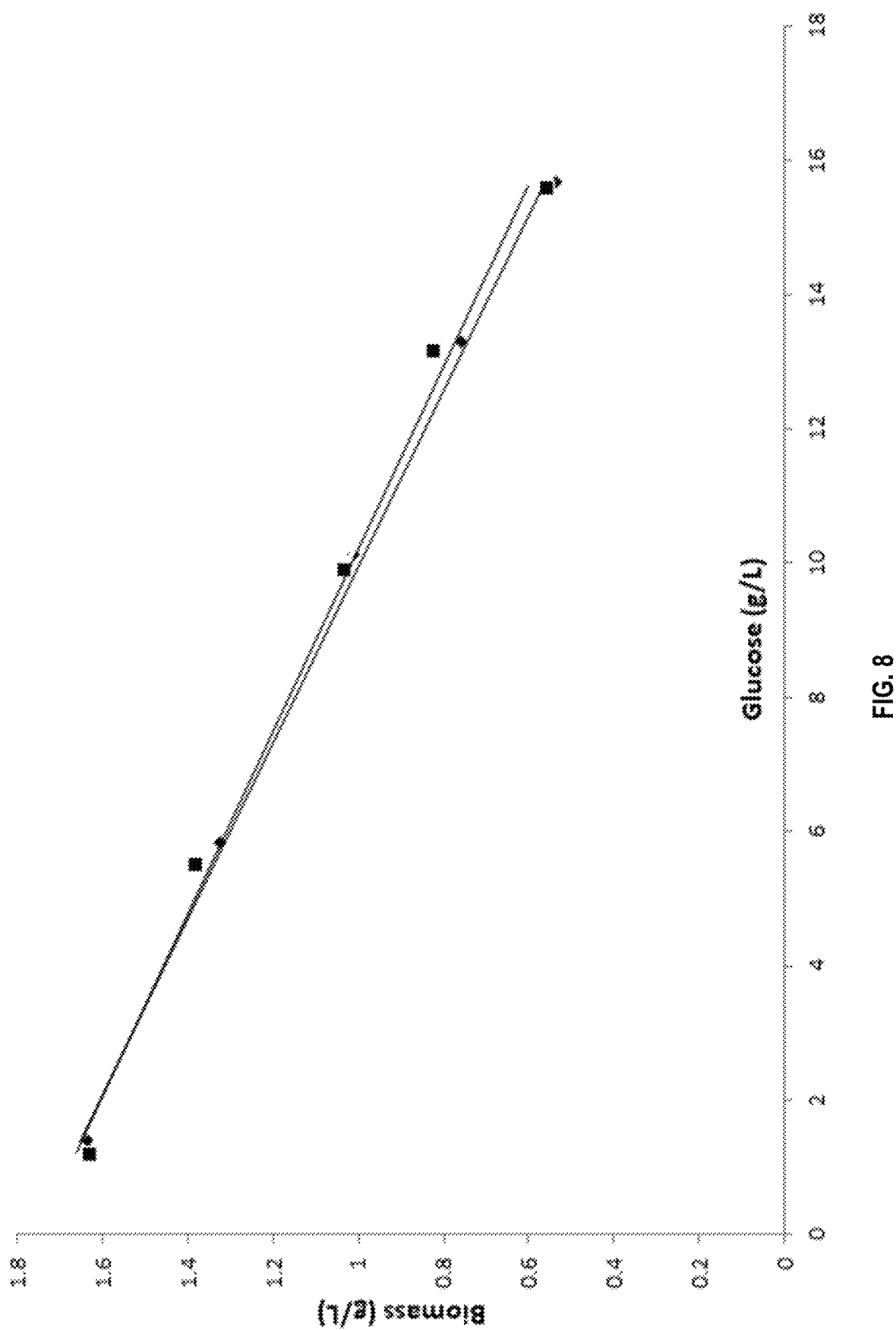
FIG. 8. Calculation of biomass yield on glucose. Plot displays biomass versus glucose concentration. Diamonds: IMX884-I. Squares: IMX884-II. The values for IMX884-I are partly overlapping with IMX884-II.
Figure 13:
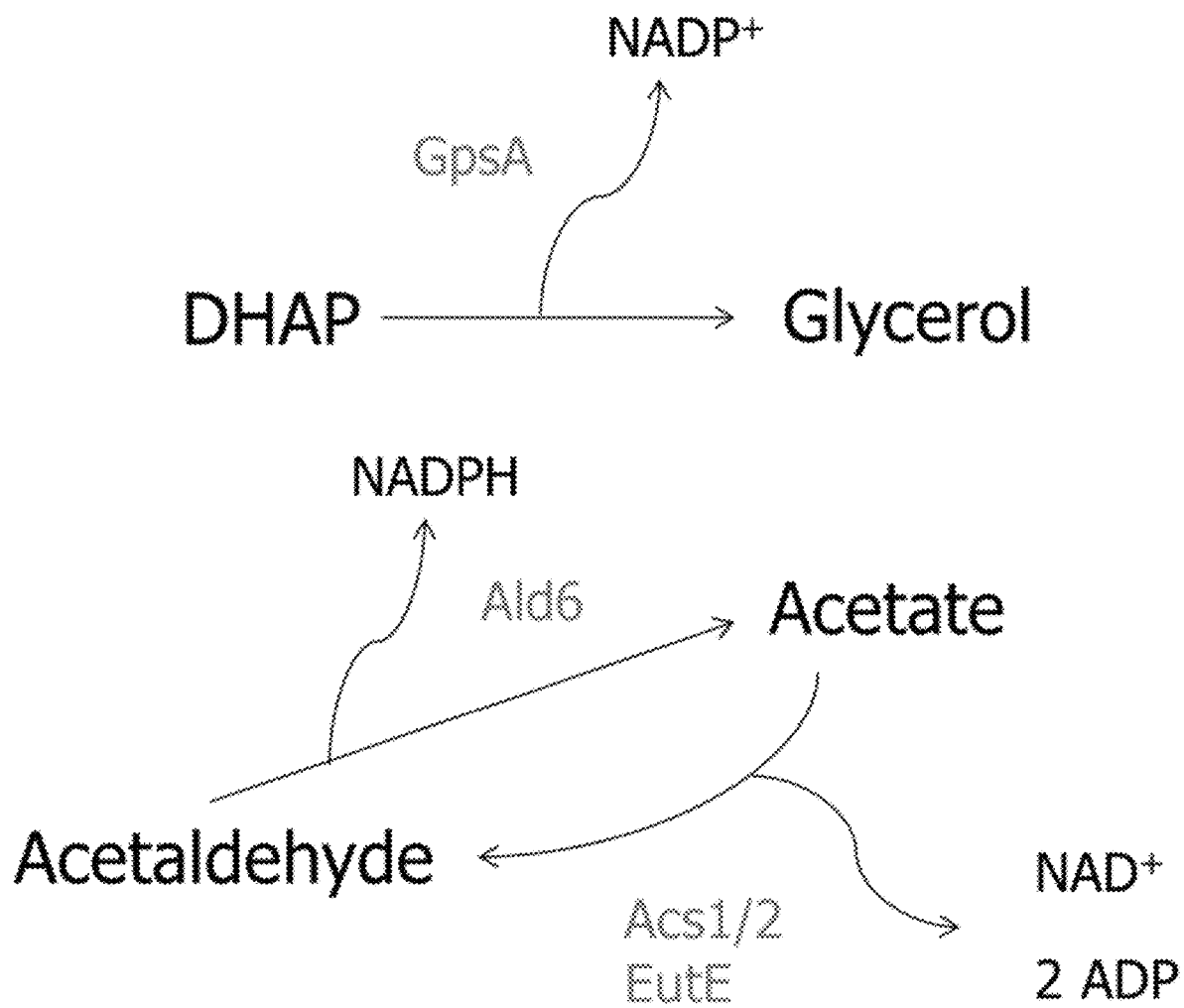
FIG. 13. Potential cytosolic transhydrogenase cycle, exchanging NADH with NADPH, catalysed by EutE, Acs1/2 and Ald6. Formed NADPH can be used for DHAP reduction to glycerol by GpsA.

Strain IMX776 showed a much lower acetate consumption in the high-glucose cultures than in low-osmolarity cultures (Tables 4 and 5). This difference could be caused by an increased flux through the cytosolic, $NADP^+$-dependent acetaldehyde dehydrogenase Ald6, coupled to the increased demand for NADPH in the cytosolic GpsA reaction. Generating NADPH via the oxidation of acetaldehyde to acetate, which can subsequently be reduced to ethanol via acetyl-CoA synthetase, EutE and $NAD^+$-dependent alcohol dehydrogenase, would result in less extracellular acetate being consumed for NADH reoxidation (FIG. 13). Deletion of ALD6 had a strong impact on the physiology of anaerobic cultures of acetate-reducing gpsA-expressing S. cerevisiae. Although the specific growth rates of strain IMX776 (gpd1::gpsA gpd2:eutE) and strain IMX901 (gpd1::gpsA gpd2:eutE ald6Δ) in high-osmolarity cultures were similar (Table 5), complete absence of a lag phase reduced the overall fermentation time of the latter strain by ca. 35 h (FIG. 12). In addition, strain IMX901 fully relied on exogenous acetic acid supply for its redox balancing. When, after exponential growth was finished, no additional acetate was provided, growth and glucose consumption slowed down considerably (FIG. 6). A similar addition of acetate to a high-osmolarity batch culture of strain IMX776 did not affect its growth (FIG. 6).

In contrast to strains IMX884 and IMX776, strain IMX901 retained a glycerol non-producing phenotype throughout growth in bioreactor cultures on high-osmolarity medium, resulting in a 13% higher ethanol yield on glucose compared to strain IMX992 (GPD1 GPD2 sga1::eutE; Table 5). This, in combination with a measured intracellular glycerol concentration of 5.3±0.04 g/L in anaerobic shake-flask cultures of strain IMX901 on high-osmolarity medium, indicated a complete intracellular retention of glycerol formed via GpsA in this strain. When additional acetate was added to high-osmolarity bioreactor cultures of strain IMX901 immediately after the exponential phase, no extracellular glycerol was detected (FIG. 12). However, when acetate was added 20 h into the stationary phase (FIG. 6), low concentrations of glycerol were detectable (<1 g/L final concentration).

TABLE 4

Figure 5:
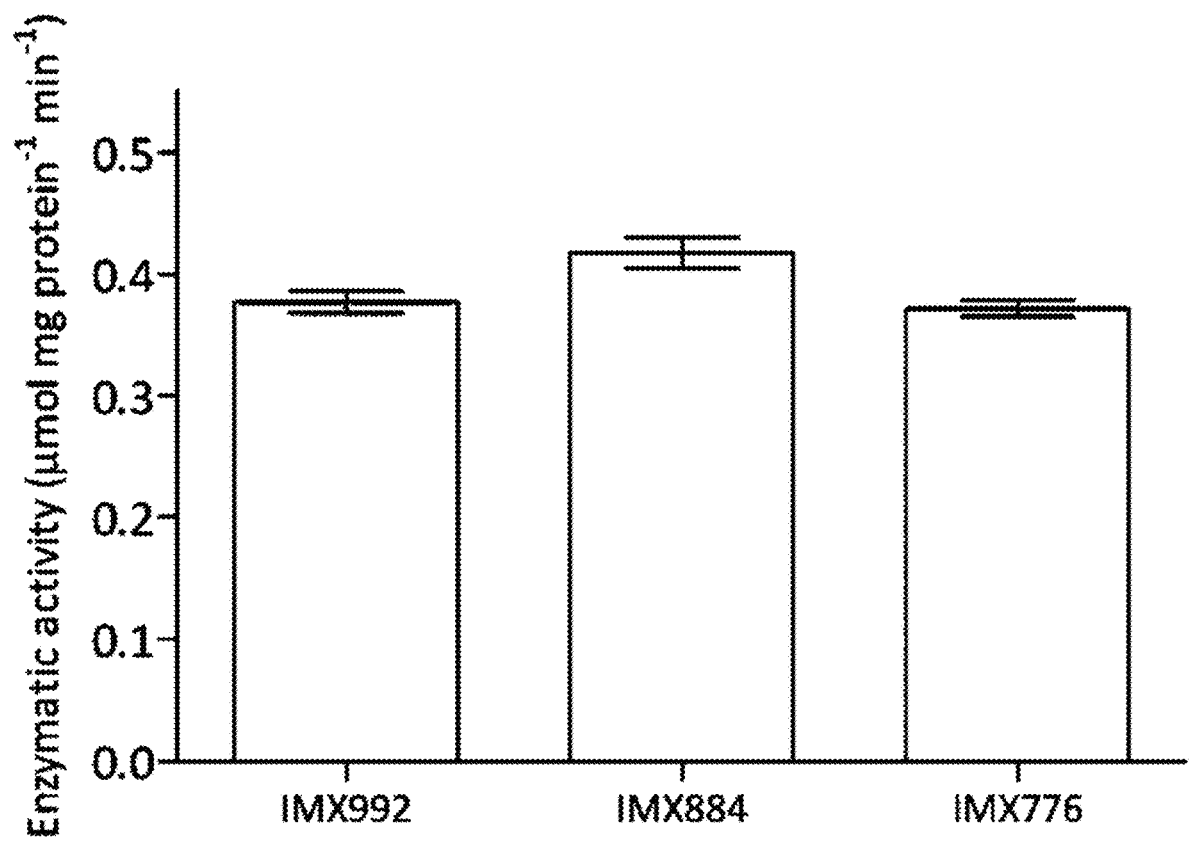
FIG. 5. Specific rates of EutE-dependent reduction of acetyl-CoA by cell extracts of shake-flask cultures on synthetic medium (20 g/L) glucose. From left to right: *S. cerevisiae* strains IMX992 (GPD1 GPD2 sga1::eutE), IMX884 (GPD1 gpd2::eutE) and IMX776 (gpd1::gpsA gpd2::eutE). Data represent averages±mean deviations of assays on independent duplicate cultures.

Specific growth rate (μ) and stoichiometric relationships between glycerol production and biomass formation, acetate consumption and glucose consumption, and acetate consumption and biomass formation in anaerobic bioreactor batch cultures of S. cerevisiae strains with different genetic modifications in glycerol and acetate metabolism. Cultures were grown on synthetic medium containing 20 g/L glucose and 3 g/L acetic acid (pH 5). Specific growth rates and stoichiometries were calculated from the mid-exponential growth phase and represent averages ± mean deviations of measurements on independent duplicate cultures. In all cultures, carbon recoveries were between 95 and 100%. Enzyme activities of acetylating acetaldehyde dehydrogenase in cell extracts of eutE-expressing strains were similar (FIG. 5). *Data on strain IMX888 were taken from (Papapetridis et al., 2016).

| Strain | IME324 | IMX992 | IMX884 | IMX776 | IMX901 | IMX888* |
|---|---|---|---|---|---|---|
| Relevant Genotype | GPD1 GPD2 | GPD1 GPD2 sga1::eutE | GPD1 gpd2::eutE | gpd1::gpsA gpd2::eutE | gpd1::gpsA gpd2::eutE ald6Δ | gpd1Δ gpd2::eutE |

TABLE 4-continued

Specific growth rate (μ) and stoichiometric relationships between glycerol production and biomass formation, acetate consumption and glucose consumption, and acetate consumption and biomass formation in anaerobic bioreactor batch cultures of *S. cerevisiae* strains with different genetic modifications in glycerol and acetate metabolism. Cultures were grown on synthetic medium containing 20 g/L glucose and 3 g/L acetic acid (pH 5). Specific growth rates and stoichiometries were calculated from the mid-exponential growth phase and represent averages ± mean deviations of measurements on independent duplicate cultures. In all cultures, carbon recoveries were between 95 and 100%. Enzyme activities of acetylating acetaldehyde dehydrogenase in cell extracts of eutE-expressing strains were similar (FIG. 5). *Data on strain IMX888 were taken from (Papapetridis et al., 2016).

| Strain | IME324 | IMX992 | IMX884 | IMX776 | IMX901 | IMX888* |
|---|---|---|---|---|---|---|
| μ (per hour) | 0.31 ± 0.01 | 0.30 ± 0.00 | 0.31 ± 0.01 | 0.24 ± 0.01 | 0.24 ± 0.01 | 0.26 ± 0.01 |
| Ratio glycerol produced/biomass (mmol/(g biomass)) | 9.19 ± 0.08 | 8.28 ± 0.14 | 1.92 ± 0.06 | <0.1 | <0.1 | <0.1 |
| Ratio acetate consumed/biomass (mmol/(g biomass)) | 2.43 ± 0.16 | 3.35 ± 0.08 | 5.77 ± 0.25 | 6.66 ± 0.01 | 6.41 ± 0.28 | 6.920 ± 0.12 |
| Ratio acetate consumed/glucose (g/g) | 0.010 ± 0.000 | 0.015 ± 0.000 | 0.026 ± 0.001 | 0.031 ± 0.001 | 0.031 ± 0.000 | 0.032 ± 0.00 |

TABLE 5

Specific growth rate (μ), yields (Y) of biomass, ethanol and glycerol on glucose and stoichiometric relationships between glycerol production and biomass formation, acetate consumption and glucose consumption, and acetate consumption and biomass formation in anaerobic bioreactor batch cultures of *S. cerevisiae* strains with different genetic modifications in glycerol and acetate metabolism. Cultures were grown on synthetic medium containing 180 g/L glucose and 3 g/L acetic acid (pH 5). Specific growth rates and stoichiometries were calculated from the mid-exponential growth phase and represent averages ± mean deviations of measurements on independent duplicate cultures.

| Strain | IMX992 | IMX884 | IMX776 | IMX901 |
|---|---|---|---|---|
| Relevant Genotype | GPD1 GPD2 sga1::eutE | GPD1 gpd2::eutE | gpd1::gpsA gpd2::eutE | gpd1::gpsA gpd2::eutE ald6Δ |
| μ (per hour) | 0.28 ± 0.02 | 0.27 ± 0.00 | 0.14 ± 0.00 | 0.12 ± 0.02 |
| γ biomass/glucose (g/g) | 0.087 ± 0.001 | 0.085 ± 0.000 | 0.089 ± 0.000 | 0.077 ± 0.013 |
| γ ethanol/glucose (g/g) | 0.43 ± 0.01 | 0.42 ± 0.02 | 0.47 ± 0.01 | 0.49 ± 0.00 |
| γ glycerol/glucose (g/g) | 0.07 ± 0.00 | 0.05 ± 0.00 | 0.02 ± 0.00 | <0.001 |
| γ glycerol/biomass (mmol (g/ biomass)) | 8.76 ± 0.25 | 6.34 ± 0.26 | 3.29 ± 0.41 | <0.1 |
| Acetate consumed/biomass (mmol/(g biomass)) | 2.67 ± 0.96 | 2.98 ± 0.08 | 2.88 ± 0.17 | 5.71 ± 0.15 |
| Acetate consumed/glucose (g/g) | 0.011 ± 0.001 | 0.015 ± 0.000 | 0.016 ± 0.000 | 0.027 ± 0.003 |

REFERENCES

Albertyn J, Hohmann S, Prior B A. Characterization of the osmotic-stress response in *Saccharomyces cerevisiae*: osmotic stress and glucose repression regulate glycerol-3-phosphate dehydrogenase independently. Curr Gen. 1994; 25:12-8.

Albertyn J, Hohmann S, Thevelein J M, Prior B A. GPD1, which encodes glycerol-3-phosphate dehydrogenase, is essential for growth under osmotic stress in *Saccharomyces cerevisiae*, and its expression is regulated by the high-osmolarity glycerol response pathway. Mol Cell Biol. 1994; 14:4135-44.

Ansell R, Granath K, Hohmann S, Thevelein J M, Adler L. The two isoenzymes for yeast $NAD^+$-dependent glycerol 3-phosphate dehydrogenase encoded by GPD1 and GPD2 have distinct roles in osmoadaptation and redox regulation. EMBO J. 1997; 16:2179-87.

Daniel Gietz R, Woods R A: Methods Enzymol. 2002; 87-96.

Entian K D, Kötter P: 25 Yeast Genetic Strain and Plasmid Collections. Methods Microbiol. 2007; 629-666.

Guadalupe-Medina V, Almering M J H, van Maris A J A, Pronk J T. Elimination of glycerol production in anaerobic cultures of a *Saccharomyces cerevisiae* strain engineered to use acetic acid as an electron acceptor. Appl Environ Microbiol. 2010; 76:190-5.

Guadalupe-Medina V, Metz B, Oud B, van Der Graaf C M, Mans R, Pronk J T, van Maris A J A. Evolutionary engineering of a glycerol-3-phosphate dehydrogenase-negative, acetate-reducing *Saccharomyces cerevisiae* strain enables anaerobic growth at high glucose concentrations. Microb Biotechnol. 2014; 7:44-53.

Mans R, van Rossum H M, Wijsman M, Backx A, Kuijpers N G, van den Broek M, Daran-Lapujade P, Pronk J T, van Maris A J, Daran J-M. CRISPR/Cas9: a molecular Swiss army knife for simultaneous introduction of multiple genetic modifications in *Saccharomyces cerevisiae*. FEMS Yeast Res. 2015; 15:fov004.

Mumberg D, Müller R, Funk M. Yeast vectors for the controlled expression of heterologous proteins in different genetic backgrounds. Gene. 1995; 156:119-22.

Papapetridis I, van Dijk M, Dobbe A P, Metz B, Pronk J T, van Maris A J A. Improving ethanol yield in acetate-reducing Saccharomyces cerevisiae by cofactor engineering of 6-phosphogluconate dehydrogenase and deletion of ALD6. Microb Cell Fact. 2016; 15:67.

Postma E, Verduyn C, Scheffers W A, van Dijken J P. Enzymic analysis of the crabtree effect in glucose-limited chemostat cultures of Saccharomyces cerevisiae. Appl Environ Microbiol. 1989; 55:468-77.

Solis-Escalante D, Kuijpers N G A, Nadine B, Bolat I, Bosman L, Pronk J T, Daran J-M, Pascale D-L. amdSYM, a new dominant recyclable marker cassette for Saccharomyces cerevisiae. FEMS Yeast Res. 2013; 13:126.

Verduyn C, Postma E, Scheffers W A, van Dijken J P. Effect of benzoic acid on metabolic fluxes in yeasts: A continuous-culture study on the regulation of respiration and alcoholic fermentation. Yeast. 1992; 8:501-17.

Wiedemann B, Boles E. Codon-optimized bacterial genes improve L-arabinose fermentation in recombinant Saccharomyces cerevisiae. Appl Environ Microbiol. 2008; 74:2043-50.

The invention claimed is:

1. A recombinant cell, optionally a recombinant yeast cell comprising:
   a) a gene encoding an enzyme having glycerol-3-phosphate dehydrogenase activity, wherein said enzyme has a cofactor dependency for at least NADP and/or for NADPH;
   b) a gene encoding an enzyme having at least NAD dependent acetylating acetaldehyde dehydrogenase activity (EC 1.2.1.10); and
   c) a mutation or disruption in at least one gene selected from the group of GPD1 and GPD2.

2. The cell according to claim 1 wherein the enzyme having glycerol-3-phosphate dehydrogenase activity has a higher affinity and/or lower Michaelis constant and/or a higher maximum activity for NADPH than for NADH.

3. The cell according to claim 1 wherein the gene encoding an enzyme having glycerol-3-phosphate dehydrogenase activity comprises at least one exogenous gene.

4. The cell according to claim 3 wherein said gene encodes an enzyme with an amino acid sequence according to SEQ ID NO: 1 or a functional homologue thereof having a sequence identity of at least 50%.

5. The cell according to claim 1 wherein the gene encoding an enzyme having at least NAD dependent acetylating acetaldehyde dehydrogenase activity encodes an enzyme with an amino acid sequence according to SEQ ID NO: 2 or a functional homologue thereof having a sequence identity of at least 50%.

6. The cell according to claim 1 which cell is free of, or has reduced NADPH-dependent aldehyde reductase activity (EC 1.2.1.4) compared to a corresponding wildtype cell thereof.

7. The cell according to claim 1 wherein the genome of said cell comprises a mutation in ALD6 or a functional homologue thereof having a sequence identity of at least 50%.

8. The cell according to claim 1 wherein the enzyme having at least $NAD^+$ dependent acetylating acetaldehyde dehydrogenase activity catalyses the reversible conversion of acetyl-CoenzymeA to acetaldehyde and the subsequent reversible conversion of acetaldehyde to ethanol.

9. The cell according to claim 8 wherein the enzyme comprises both NAD dependent acetylating acetaldehyde dehydrogenase (EC 1.2.1.10) activity and NAD dependent alcohol dehydrogenase activity (EC 1.1.1.1).

10. The cell according to claim 1 wherein the gene encoding an enzyme having at least NAD dependent acetylating acetaldehyde dehydrogenase activity encodes an enzyme with an amino acid sequence according to SEQ ID NO: 3 or a functional homologue thereof having a sequence identity of at least 50%.

11. The cell according to claim 1 which does not comprise a gene encoding an enzyme having pyruvate formate lyase activity.

12. The cell according to claim 1 for the preparation of ethanol, butanol, lactic acid, succinic acid, a plastic, an organic acid, a solvent, an animal feed supplement, a pharmaceutical, a vitamin, an amino acid, an enzyme or a chemical feedstock, optionally ethanol.

13. A process for preparing a fermentation product, optionally ethanol, comprising preparing a fermentation product from a fermentable carbohydrate, optionally selected from the group of glucose, fructose, sucrose, maltose, xylose, arabinose, galactose, cellobiose and mannose which wherein said preparing is carried out under anaerobic conditions by contacting a cell according to claim 1 with said fermentable carbohydrate.

14. The process according to claim 13, wherein fermentable carbohydrate is obtained from starch, lignocellulose, and/or pectin.

15. The process according to claim 13, wherein the concentration of glucose is 80 g/L or more.

* * * * *